US005710278A

United States Patent [19]

Goto et al.

[11] Patent Number: 5,710,278

[45] Date of Patent: Jan. 20, 1998

[54] HERBICIDAL 1-PYRIDYLTETRAZOLINONES

[75] Inventors: Toshio Goto; Koichi Moriya, both of Tochigi; Fritz Maurer, Tokyo; Seishi Ito, Oyama; Katsuaki Wada, Tochigi; Kazuhiro Ukawa, Oyama; Ryo Watanabe; Asami Ito, both of Tochigi, all of Japan

[73] Assignee: Nihon Bayer Agrochem K.K., Tokyo, Japan

[21] Appl. No.: 802,152

[22] Filed: Feb. 19, 1997

Related U.S. Application Data

[62] Division of Ser. No. 498,736, Jun. 6, 1995, Pat. No. 5,641,727.

[30] Foreign Application Priority Data

Jul. 12, 1994 [JP] Japan .................................... 6-181916
Jan. 30, 1995 [JP] Japan .................................... 7-31785

[51] Int. Cl.[6] .................................... C07D 401/04
[52] U.S. Cl. .................................... 546/268.4
[58] Field of Search .................................... 546/268.4

[56] References Cited

U.S. PATENT DOCUMENTS

| | | | |
|---|---|---|---|
| 4,618,365 | 10/1986 | Covey et al. | 548/251 |
| 4,826,529 | 5/1989 | Covey et al. | 548/251 |
| 4,830,661 | 5/1989 | Covey et al. | 504/261 |
| 4,885,026 | 12/1989 | Lee et al. | 546/268.4 |
| 4,956,469 | 9/1990 | Covey et al. | 548/251 |
| 5,003,075 | 3/1991 | Covey et al. | 548/251 |
| 5,019,152 | 5/1991 | Covey et al. | 548/251 |
| 5,342,954 | 8/1994 | Goto et al. | 504/261 |
| 5,344,814 | 9/1994 | Goto et al. | 504/261 |
| 5,347,009 | 9/1994 | Goto et al. | 504/261 |
| 5,347,010 | 9/1994 | Goto et al. | 504/261 |
| 5,362,704 | 11/1994 | Goto et al. | 504/134 |

*Primary Examiner*—Jane Fan
*Attorney, Agent, or Firm*—Sprung Kramer Schaefer & Briscoe

[57] ABSTRACT

Herbicidal tetrazolinone derivatives of the formula:

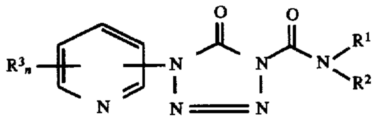

in which $R^1$ is alkyl, haloalkyl, cycloalkyl, alkenyl, haloalkenyl, alkynyl or phenyl, and $R^2$ is alkyl, haloalkyl, cycloalkyl, alkenyl, haloalkenyl, alkynyl or phenyl, or $R^1$ and $R^2$ together with the nitrogen atom to which they are bonded form an optionally benzofused heterocyclic ring, which is optionally substituted by $C_{1-4}$ alkyl, n is 0, 1, 2 or 3, and $R^3$ each independently is nitro, halogen, alkyl, haloalkyl, alkylthio or phenoxy.

3 Claims, No Drawings

HERBICIDAL 1-PYRIDYLTETRAZOLINONES

This application is a divisional of application Ser. No. 08/498,736, filed Jul. 6, 1995, now U.S. Pat. No. 5,641,727.

The present invention relates to tetrazolinone derivatives, to processes for their preparation and to their use as herbicides, as well as to intermediates therefor.

It has already been known that tetrazolinone derivatives are useful as herbicides (see U.S. Pat. Nos. 4,618,365; 4,826,529; 4,830,661; 4,956,469; 5,003,075; 5,019,152; 5,342,954; 5,344,814; 5,347,009; 5,347,010 and 5,362,704). There have been found novel tetrazolinone derivatives of the formula (I)

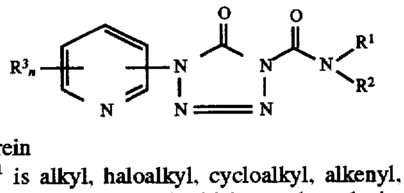

(I)

wherein $R^1$ is alkyl, haloalkyl, cycloalkyl, alkenyl, haloalkenyl, alkynyl or phenyl which may be substituted, and $R^2$ is alkyl, haloalkyl, cycloalkyl, alkenyl, haloalkenyl, alkynyl or phenyl which may be substituted, or $R^1$ and $R^2$ may form, together with the nitrogen atom to which $R^1$ and $R^2$ are bonded, a 5- or 6-membered heterocyclic ring, said heterocyclic ring may be benzofused and may be substituted by one or more $C_{1-4}$ alkyl radicals, $R^3$ is nitro, halogen, alkyl, haloalkyl, alkoxy, haloalkoxy, alkylthio or phenoxy, and n is 0, 1, 2 or 3, and when n is 2 or 3, then $R^3$ may be same or different.

The novel tetrazolinone derivatives of the formula (I) are obtained when (a) compounds of the following formula (II)

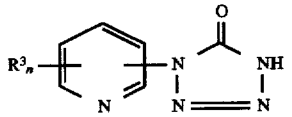

(II)

wherein $R^3$ and n have the above mentioned meanings, are reacted with compounds of the following formula (III)

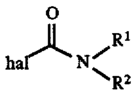

(III)

wherein $R^1$ and $R^2$ have the above mentioned meanings, and hal represents a releasable group such as chlorine or bromine, in the presence of acid-binder, in the presence of inert solvents.

The novel tetrazolinone derivatives of the formula (I) exhibit powerful herbicidal properties.

Surprisingly, the tetrazolinone derivatives of the formula (I) according to the present invention exhibit a substantially higher herbicidal activity than those known from the prior an, for instance, the aforementioned U.S. Pat. Nos. 4,618,365; 4,826,529; 4,830,661; 4,956,469; 5,003,075; 5,019,152; 5,342,954; 5,344,814; 5,347,009; 5,347,010 and 5,362,704.

In the compounds of the formula (I) according to the invention, and the respective general formulae representing their intermediates employed for the production of the compounds formula (I), each of the halogen as well as the halogen parts of the haloalkyl, haloalkenyl and haloalkoxy represent fluorine, chlorine, bromine or iodine, preferably chlorine or fluorine.

Alkyl is, for example, methyl, ethyl, propyl, isopropyl, n-(iso-, sec-, tert-)butyl, n-(iso-, sec-, tert-, neo-)pentyl or n-(iso-, sec-, tert-, neo-)hexyl.

Haloalkyl is the above mentioned alkyl groups substituted with the same or different halogen atoms, such as for example, trifluoromethyl, 2-chloroethyl and 2,2,2-trifluoroethyl.

Cycloalkyl is, for example, cyclopropyl, cyclobutyl, cyclopentyl, cyclohexyl, cycloheptyl or cyclooctyl.

Alkenyl is, for example, vinyl, allyl, isopropenyl, 1-methyl-2-propenyl, 2-methyl-2-propenyl, 2-(or 3-)butenyl or 2-(3- or 4-)pentenyl.

Haloalkenyl is the above mentioned alkenyl groups substituted with the stone or different halogen atoms, such as for example, 2-Chloro-2-propenyl.

The alkynyl represents, for example, propargyl.

The 5- or 6-membered heterocyclic ring contains, as a hetero-atom, at least one nitrogen and may contain further hetero-atoms selected from the group consisting of nitrogen, oxygen and sulfur. Said heterocyclic group may be benzofused, and for example, pyrrolidinyl, 2,5-dimethylpyrrolidinyl, pyrrolinyl, 2,5-dimethyl-3-pyrrolinyl, imidazolidinyl, pyrazolidinyl, pyrazolinyl, piperidyl, 2-methylpiperidyl, 2,6-dimethylpiperidyl, piperazinyl, indolinyl, morpholinyl, 1,2,3,4-tetrahydroquinolyl or 2-methyl-1,2,3,4-tetrahydroquinolyl can be exemplified.

Phenyl and phenoxy may optionally be substituted. The substituent(s) are selected from the group consisting of halogen, cyano, nitro, alkyl, haloalkyl, alkoxy, haloalkoxy and alkylthio.

Alkoxy is for example, methoxy, ethoxy, propoxy, isopropoxy, n-(iso-, sec-, tert-)butoxy, n-(iso-, sec-, tert-, neo-)pentoxy or n-(iso-, sec-, tert-, neo-)hextoxy.

Alkylthio is, for example, methylthio, ethylthio, propylthio, isopropylthio, n-(iso-, sec-, tert-)butylthio, n-(iso-, sec-, tert-, neo-)pentylthio or n-(iso-, sec-, tert-, neo-)hexylthio.

Haloalkoxy is the above mentioned alkoxy substituted with the stone or different halogen atoms, for example, trifluoromethoxy.

Among the tetrazolinone derivatives according to the invention, of the formula (I), preferred compounds are those in which $R^1$ is $C_{1-6}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynl or phenyl, and $R^2$ is $C_{1-6}$ alkyl, $C_{1-6}$ haloalkyl, $C_{3-8}$ cycloalkyl, $C_{2-6}$ alkenyl, $C_{2-6}$ haloalkenyl, $C_{3-6}$ alkynyl or phenyl, or $R^1$ and $R^2$ may form, together with the nitrogen atom to which $R^1$ and $R^2$ are bonded, a 5- or 6-membered heterocyclic ring, the hetero atoms of which are selected from the group consisting of nitrogen atom, oxygen and sulfur and said heterocyclic ring may be benzofused and may be substituted by one or more methyl radicals, $R^3$ is nitro, fluoro, chloro, bromo, $C_{1-4}$ alkyl, $C_{1-4}$ haloalkyl, $C_{1-4}$ alkoxy, $C_{1-4}$ haloalkoxy, $C_{1-4}$ alkylthio or phenoxy, and n is 0, 1, 2 or 3, and when n is 2 or 3, $R^3$ may be same or different.

Particularly preferred tetrazolinone derivatives of the formula (I) are those in which $R^1$ is $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl or phenyl, and $R^2$ is $C_{1-4}$ alkyl, $C_{1-4}$ haloalkyl, cyclopropyl, cyclopentyl, cyclohexyl, $C_{2-4}$ alkenyl, $C_{2-4}$ haloalkenyl, $C_{3-4}$ alkynyl or phenyl, or $R^1$ and $R^2$ may form, together with the nitrogen atom to which $R^1$ and $R^2$ are bonded, pyrrolidinyl, 2,5-dimethylpyrrolidinyl, pyrrolinyl, 2,5-dimethyl-3-pyrrolinyl, piperidyl, 2-methylpiperidyl, 2,6-dimethylpiperidyl, piperazinyl, morpholinyl, 1,2,3,4-tetrahydroquinolyl or 2-methyl-1,2,3,4-tetrahydroquinolyl.

$R^3$ is nitro, fluoro, chloro, bromo, $C_{1-4}$ alkyl, $C_{1-4}$ haloalkyl, $C_4$ alkoxy, $C_4$ haloalkoxy, $C_{1-4}$ alkylthio or phenoxy, and n is 0, 1 or 2, and when n is 2, $R^3$ may be same or different.

Specifically, compounds according to the invention wherein $R^1$ and $R^2$ represent each an independent group are shown in the Table 1, and those wherein $R^1$ and $R^2$ together with the nitrogen to which they are bonded form a heterocyclic ring are shown in the Table 2.

In the Tables 1, 2 and 3,

Q1 is 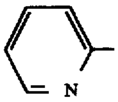, Q2 is 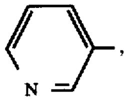,

Q3 is 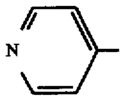, Q4 is 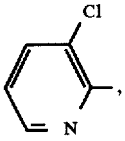,

Q5 is 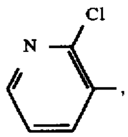, Q6 is 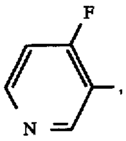,

Q7 is 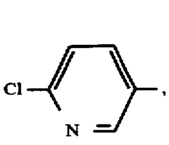, Q8 is 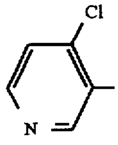,

Q9 is 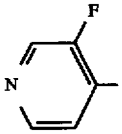, Q10 is 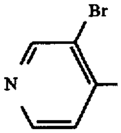,

Q11 is 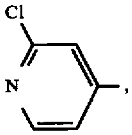, Q12 is 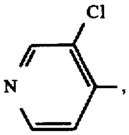,

Q13 is 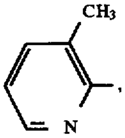, Q14 is 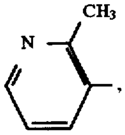,

-continued

Q15 is 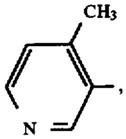, Q16 is 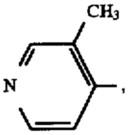,

Q17 is 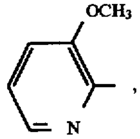, Q18 is 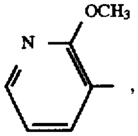,

Q19 is 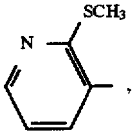, Q20 is 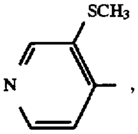,

Q21 is 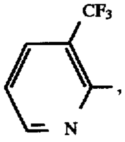, Q22 is 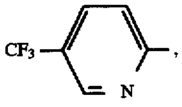,

Q23 is 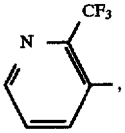, Q24 is 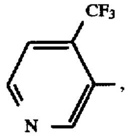,

Q25 is 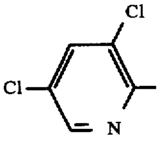, Q26 is 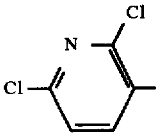,

Q27 is 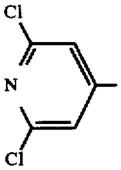, Q28 is 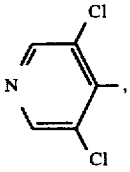,

Q29 is 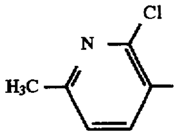, Q30 is 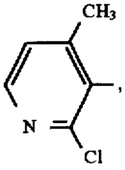,

Q31 is 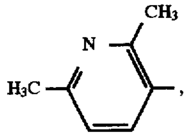, Q32 is 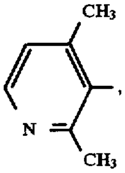,

Q33 is 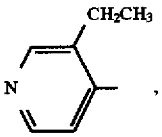, Q34 is 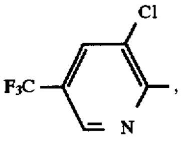,

-continued

Q35 is 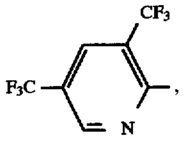, Q36 is 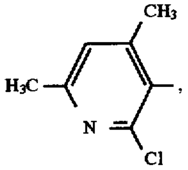,

Q37 is 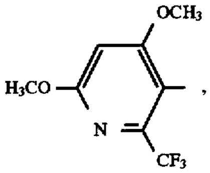, Q38 is 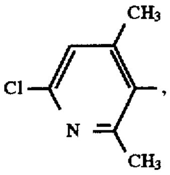,

Q39 is 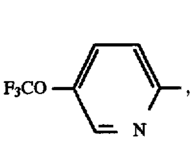, Q40 is 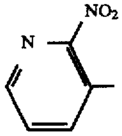 and

Q41 is 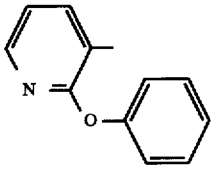

TABLE 1

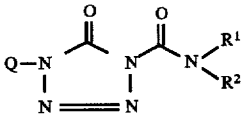

| Q | $R^1$ | $R^2$ |
|---|---|---|
| Q1 | methyl | isopropyl |
| Q1 | methyl | cyclopropyl |
| Q1 | ethyl | ethyl |
| Q1 | ethyl | isopropyl |
| Q1 | ethyl | cyclopropyl |
| Q1 | ethyl | cyclohexyl |
| Q1 | n-propyl | isopropyl |
| Q1 | isopropyl | isopropyl |
| Q1 | isopropyl | phenyl |
| Q2 | methyl | ethyl |
| Q2 | methyl | isopropyl |
| Q2 | methyl | cyclopropyl |
| Q2 | ethyl | ethyl |
| Q2 | ethyl | isopropyl |
| Q2 | ethyl | cyclopropyl |
| Q2 | n-propyl | cyclopropyl |
| Q2 | isopropyl | isopropyl |
| Q2 | isopropyl | cyclohexyl |
| Q3 | methyl | methyl |
| Q3 | methyl | isopropyl |
| Q3 | methyl | cyclopropyl |
| Q3 | ethyl | ethyl |
| Q3 | ethyl | n-propyl |
| Q3 | ethyl | isopropyl |
| Q3 | ethyl | cyclohexyl |
| Q3 | n-propyl | isopropyl |
| Q3 | isopropyl | isopropyl |
| Q3 | isopropyl | phenyl |
| Q4 | methyl | n-propyl |
| Q4 | methyl | isopropyl |
| Q4 | methyl | cyclopropyl |
| Q4 | methyl | cyclohexyl |
| Q4 | methyl | 1-methyl-2-propenyl |
| Q4 | ethyl | ethyl |

TABLE 1-continued

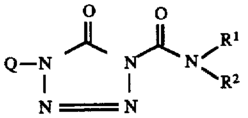

| Q | $R^1$ | $R^2$ |
|---|---|---|
| Q4 | ethyl | isopropyl |
| Q4 | ethyl | cyclopropyl |
| Q4 | ethyl | cyclohexyl |
| Q4 | 2-chloroethyl | isopropyl |
| Q4 | 2-chloroethyl | 2-chloroethyl |
| Q4 | isopropyl | 2,2,2-trifluoroethyl |
| Q4 | n-propyl | isopropyl |
| Q4 | n-propyl | cyclopropyl |
| Q4 | n-propyl | cyclohexyl |
| Q4 | isopropyl | isopropyl |
| Q4 | isopropyl | phenyl |
| Q4 | isopropyl | propargyl |
| Q4 | allyl | allyl |
| Q4 | propargyl | propargyl |
| Q4 | isopropyl | allyl |
| Q5 | methyl | methyl |
| Q5 | methyl | ethyl |
| Q5 | methyl | n-propyl |
| Q5 | methyl | isopropyl |
| Q5 | methyl | cyclopropyl |
| Q5 | methyl | 1-methyl-2-propenyl |
| Q5 | methyl | cyclopentyl |
| Q5 | ethyl | ethyl |
| Q5 | ethyl | n-propyl |
| Q5 | ethyl | isopropyl |
| Q5 | ethyl | sec-butyl |
| Q5 | ethyl | cyclopropyl |
| Q5 | ethyl | cyclohexyl |
| Q5 | ethyl | 2,2,2-trifluoroethyl |
| Q5 | n-propyl | 2,2,2-trifluoroethyl |
| Q5 | isopropyl | 2,2,2-trifluoroethyl |
| Q5 | 2-chloroethyl | ethyl |
| Q5 | 2-chloroethyl | n-propyl |
| Q5 | 2-chloroethyl | isopropyl |
| Q5 | 2-chloroethyl | 2-chloroethyl |
| Q5 | n-propyl | isopropyl |
| Q5 | n-propyl | cyclopropyl |
| Q5 | n-propyl | cyclohexyl |
| Q5 | isopropyl | isopropyl |
| Q5 | isopropyl | phenyl |
| Q5 | isopropyl | allyl |
| Q5 | isopropyl | 2-chloro-2-propenyl |
| Q5 | isopropyl | 2-methyl-2-propenyl |
| Q5 | isopropyl | propargyl |
| Q5 | allyl | allyl |
| Q5 | propargyl | propargyl |
| Q6 | methyl | methyl |
| Q6 | methyl | isopropyl |
| Q6 | methyl | cyclopropyl |
| Q6 | methyl | cyclopentyl |
| Q6 | methyl | 1-methyl-2-propenyl |
| Q6 | ethyl | ethyl |
| Q6 | ethyl | isopropyl |
| Q6 | ethyl | cyclopropyl |
| Q6 | ethyl | cyclohexyl |
| Q6 | isopropyl | 2,2,2-trifluoroethyl |
| Q6 | 2-chloroethyl | isopropyl |
| Q6 | 2-chloroethyl | 2-chloroethyl |
| Q6 | n-propyl | isopropyl |
| Q6 | n-propyl | cyclopropyl |
| Q6 | n-propyl | cyclopentyl |
| Q6 | isopropyl | isopropyl |
| Q6 | isopropyl | cyclohexyl |
| Q6 | isopropyl | phenyl |
| Q6 | isopropyl | allyl |
| Q6 | isopropyl | propargyl |
| Q6 | allyl | allyl |
| Q6 | propargyl | propargyl |
| Q7 | methyl | isopropyl |
| Q7 | methyl | cyclopropyl |

TABLE 1-continued

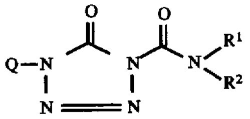

| Q | $R^1$ | $R^2$ |
|---|---|---|
| Q7 | ethyl | ethyl |
| Q7 | ethyl | isopropyl |
| Q7 | ethyl | cyclopropyl |
| Q7 | n-propyl | isopropyl |
| Q7 | isopropyl | isopropyl |
| Q7 | isopropyl | phenyl |
| Q8 | methyl | methyl |
| Q8 | methyl | isopropyl |
| Q8 | methyl | cyclopropyl |
| Q8 | methyl | cyclohexyl |
| Q8 | methyl | 1-methyl-2-propenyl |
| Q8 | ethyl | ethyl |
| Q8 | ethyl | isopropyl |
| Q8 | ethyl | cyclopropyl |
| Q8 | ethyl | cyclopentyl |
| Q8 | ethyl | 2,2,2-trifluoroethyl |
| Q8 | n-propyl | 2,2,2-trifluoroethyl |
| Q8 | iso-propyl | 2,2,2-trifluoroethyl |
| Q8 | 2-chloroethyl | ethyl |
| Q8 | 2-chloroethyl | n-propyl |
| Q8 | 2-chloroethyl | isopropyl |
| Q8 | 2-chloroethyl | 2-chloroethyl |
| Q8 | n-propyl | isopropyl |
| Q8 | n-propyl | cyclopropyl |
| Q8 | n-propyl | cyclohexyl |
| Q8 | isopropyl | isopropyl |
| Q8 | isopropyl | phenyl |
| Q8 | isopropyl | allyl |
| Q8 | isopropyl | 2-chloro-2-propenyl |
| Q8 | isopropyl | 2-methyl-2-propenyl |
| Q8 | isopropyl | propargyl |
| Q8 | allyl | allyl |
| Q8 | propargyl | propargyl |
| Q9 | methyl | ethyl |
| Q9 | methyl | isopropyl |
| Q9 | methyl | cyclopropyl |
| Q9 | methyl | s-butyl |
| Q9 | methyl | 1-methyl-2-propenyl |
| Q9 | ethyl | ethyl |
| Q9 | ethyl | n-propyl |
| Q9 | ethyl | isopropyl |
| Q9 | ethyl | cyclopropyl |
| Q9 | isopropyl | 2,2,2-trifluoroethyl |
| Q9 | 2-chloroethyl | isopropyl |
| Q9 | 2-chloroethyl | 2-chloroethyl |
| Q9 | n-propyl | isopropyl |
| Q9 | n-propyl | cyclopropyl |
| Q9 | n-propyl | s-butyl |
| Q9 | isopropyl | isopropyl |
| Q9 | isopropyl | cyclohexyl |
| Q9 | isopropyl | phenyl |
| Q9 | isopropyl | allyl |
| Q9 | isopropyl | propargyl |
| Q9 | allyl | allyl |
| Q9 | propargyl | propargyl |
| Q10 | methyl | n-propyl |
| Q10 | methyl | isopropyl |
| Q10 | methyl | cyclopropyl |
| Q10 | methyl | s-butyl |
| Q10 | methyl | 1-methyl-2-propenyl |
| Q10 | ethyl | ethyl |
| Q10 | ethyl | n-propyl |
| Q10 | ethyl | isopropyl |
| Q10 | ethyl | cyclopropyl |
| Q10 | ethyl | phenyl |
| Q10 | isopropyl | 2,2,2-trifluoroethyl |
| Q10 | 2-chloroethyl | isopropyl |
| Q10 | 2-chloroethyl | 2-chloroethyl |
| Q10 | n-propyl | isopropyl |
| Q10 | n-propyl | cyclopropyl |

TABLE 1-continued

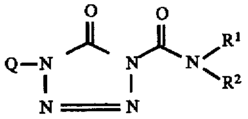

| Q | $R^1$ | $R^2$ |
|---|---|---|
| Q10 | n-propyl | s-butyl |
| Q10 | isopropyl | cyclohexyl |
| Q10 | isopropyl | phenyl |
| Q10 | isopropyl | allyl |
| Q10 | isopropyl | propargyl |
| Q10 | allyl | allyl |
| Q10 | propargyl | propargyl |
| Q11 | methyl | isopropyl |
| Q11 | ethyl | ethyl |
| Q11 | ethyl | isopropyl |
| Q11 | ethyl | s-butyl |
| Q11 | ethyl | phenyl |
| Q11 | n-propyl | isopropyl |
| Q11 | isopropyl | phenyl |
| Q12 | methyl | n-propyl |
| Q12 | methyl | isopropyl |
| Q12 | methyl | cyclopropyl |
| Q12 | methyl | 1-methyl-2-propenyl |
| Q12 | ethyl | ethyl |
| Q12 | ethyl | isopropyl |
| Q12 | ethyl | cyclopropyl |
| Q12 | ethyl | cyclohexyl |
| Q12 | isopropyl | 2,2,2-trifluoroethyl |
| Q12 | 2-chloroethyl | isopropyl |
| Q12 | 2-chloroethyl | 2-chloroethyl |
| Q12 | n-propyl | isopropyl |
| Q12 | n-propyl | cyclopropyl |
| Q12 | n-propyl | cyclohexyl |
| Q12 | isopropyl | isopropyl |
| Q12 | isopropyl | phenyl |
| Q12 | isopropyl | allyl |
| Q12 | isopropyl | propargyl |
| Q12 | allyl | allyl |
| Q12 | propargyl | propargyl |
| Q13 | methyl | isopropyl |
| Q13 | methyl | cyclopropyl |
| Q13 | methyl | cyclohexyl |
| Q13 | methyl | 1-methyl-2-propenyl |
| Q13 | ethyl | ethyl |
| Q13 | ethyl | isopropyl |
| Q13 | ethyl | cyclopropyl |
| Q13 | ethyl | cyclohexyl |
| Q13 | isopropyl | 2,2,2-trifluoroethyl |
| Q13 | 2-chloroethyl | isopropyl |
| Q13 | 2-chloroethyl | 2-chloroethyl |
| Q13 | n-propyl | isopropyl |
| Q13 | n-propyl | cyclopropyl |
| Q13 | isopropyl | isopropyl |
| Q13 | isopropyl | phenyl |
| Q13 | isopropyl | allyl |
| Q13 | isopropyl | propargyl |
| Q13 | allyl | allyl |
| Q13 | propargyl | propargyl |
| Q14 | methyl | methyl |
| Q14 | methyl | ethyl |
| Q14 | methyl | n-propyl |
| Q14 | methyl | isopropyl |
| Q14 | methyl | cyclopropyl |
| Q14 | methyl | cyclopentyl |
| Q14 | methyl | 1-methyl-2-propenyl |
| Q14 | ethyl | ethyl |
| Q14 | ethyl | n-propyl |
| Q14 | ethyl | sec-butyl |
| Q14 | ethyl | isopropyl |
| Q14 | ethyl | cyclopropyl |
| Q14 | ethyl | cyclohexyl |
| Q14 | ethyl | 2,2,2-trifluoroethyl |
| Q14 | n-propyl | 2,2,2-trifluoroethyl |
| Q14 | isopropyl | 2,2,2-trifluoroethyl |
| Q14 | 2-chloroethyl | ethyl |

TABLE 1-continued

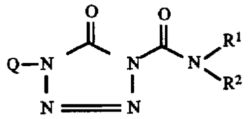

| Q | R¹ | R² |
|---|---|---|
| Q14 | 2-chloroethyl | n-propyl |
| Q14 | 2-chloroethyl | isopropyl |
| Q14 | 2-chloroethyl | 2-chloroethyl |
| Q14 | n-propyl | isopropyl |
| Q14 | n-propyl | cyclopropyl |
| Q14 | isopropyl | isopropyl |
| Q14 | isopropyl | 2-chloro-2-propenyl |
| Q14 | isopropyl | 2-methyl-2-propenyl |
| Q14 | isopropyl | propargyl |
| Q14 | isopropyl | phenyl |
| Q14 | isopropyl | allyl |
| Q14 | allyl | allyl |
| Q14 | propargyl | propargyl |
| Q15 | methyl | isopropyl |
| Q15 | methyl | cyclopropyl |
| Q15 | methyl | 1-methyl-2-propenyl |
| Q15 | ethyl | ethyl |
| Q15 | ethyl | isopropyl |
| Q15 | ethyl | cyclopropyl |
| Q15 | ethyl | cyclohexyl |
| Q15 | isopropyl | 2,2,2-trifluoroethyl |
| Q15 | 2-chloroethyl | isopropyl |
| Q15 | 2-chloroethyl | 2-chloroethyl |
| Q15 | n-propyl | isopropyl |
| Q15 | n-propyl | cyclopropyl |
| Q15 | isopropyl | isopropyl |
| Q15 | isopropyl | phenyl |
| Q15 | isopropyl | allyl |
| Q15 | isopropyl | propargyl |
| Q15 | allyl | allyl |
| Q15 | propargyl | propargyl |
| Q16 | methyl | isopropyl |
| Q16 | methyl | cyclopropyl |
| Q16 | methyl | 1-methyl-2-propenyl |
| Q16 | ethyl | ethyl |
| Q16 | ethyl | isopropyl |
| Q16 | ethyl | cyclopropyl |
| Q16 | ethyl | cyclohexyl |
| Q16 | isopropyl | 2,2,2-trifluoroethyl |
| Q16 | 2-chloroethyl | isopropyl |
| Q16 | 2-chloroethyl | 2-chloroethyl |
| Q16 | n-propyl | isopropyl |
| Q16 | n-propyl | cyclopropyl |
| Q16 | isopropyl | isopropyl |
| Q16 | isopropyl | phenyl |
| Q16 | isopropyl | allyl |
| Q16 | isopropyl | propargyl |
| Q16 | allyl | allyl |
| Q16 | propargyl | propargyl |
| Q17 | methyl | isopropyl |
| Q17 | methyl | cyclopropyl |
| Q17 | n-propyl | isopropyl |
| Q17 | methyl | 1-methyl-2-propenyl |
| Q17 | ethyl | ethyl |
| Q17 | ethyl | isopropyl |
| Q17 | ethyl | cyclopropyl |
| Q17 | isopropyl | 2,2,2-trifluoroethyl |
| Q17 | 2-chloroethyl | isopropyl |
| Q17 | 2-chloroethyl | 2-chloroethyl |
| Q17 | n-propyl | cyclopropyl |
| Q17 | isopropyl | isopropyl |
| Q17 | isopropyl | phenyl |
| Q17 | isopropyl | allyl |
| Q17 | isopropyl | propargyl |
| Q17 | allyl | allyl |
| Q17 | propargyl | propargyl |
| Q18 | methyl | isopropyl |
| Q18 | methyl | cyclopropyl |
| Q18 | methyl | phenyl |
| Q18 | methyl | 1-methyl-2-propenyl |

TABLE 1-continued

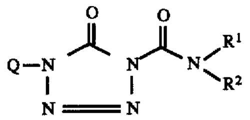

| Q | R¹ | R² |
|---|---|---|
| Q18 | ethyl | ethyl |
| Q18 | ethyl | n-propyl |
| Q18 | ethyl | isopropyl |
| Q18 | ethyl | cyclopropyl |
| Q18 | isopropyl | 2,2,2-trifluoroethyl |
| Q18 | 2-chloroethyl | isopropyl |
| Q18 | 2-chloroethyl | 2-chloroethyl |
| Q18 | n-propyl | isopropyl |
| Q18 | isopropyl | isopropyl |
| Q18 | isopropyl | phenyl |
| Q18 | isopropyl | allyl |
| Q18 | isopropyl | propargyl |
| Q18 | allyl | allyl |
| Q18 | propargyl | propargyl |
| Q19 | methyl | methyl |
| Q19 | methyl | ethyl |
| Q19 | methyl | isopropyl |
| Q19 | methyl | cyclopropyl |
| Q19 | methyl | 1-methyl-2-propenyl |
| Q19 | ethyl | ethyl |
| Q19 | ethyl | isopropyl |
| Q19 | ethyl | cyclopropyl |
| Q19 | ethyl | 2,2,2-trifluoroethyl |
| Q19 | n-propyl | 2,2,2-trifluoroethyl |
| Q19 | isopropyl | 2,2,2-trifluoroethyl |
| Q19 | 2-chloroethyl | ethyl |
| Q19 | 2-chloroethyl | n-propyl |
| Q19 | 2-chloroethyl | isopropyl |
| Q19 | 2-chloroethyl | 2-chloroethyl |
| Q19 | n-propyl | isopropyl |
| Q19 | isopropyl | isopropyl |
| Q19 | isopropyl | phenyl |
| Q19 | isopropyl | allyl |
| Q19 | isopropyl | 2-chloro-propenyl |
| Q19 | isopropyl | 2-methyl-propenyl |
| Q19 | isopropyl | propargyl |
| Q19 | allyl | allyl |
| Q19 | propargyl | propargyl |
| Q20 | methyl | isopropyl |
| Q20 | methyl | 1-methyl-2-propenyl |
| Q20 | ethyl | ethyl |
| Q20 | ethyl | isopropyl |
| Q20 | ethyl | cyclopropyl |
| Q20 | 2-chloroethyl | isopropyl |
| Q20 | 2-chloroethyl | 2-chloroethyl |
| Q20 | isopropyl | 2,2,2-trifluoroethyl |
| Q20 | n-propyl | isopropyl |
| Q20 | n-propyl | cyclopropyl |
| Q20 | isopropyl | isopropyl |
| Q20 | isopropyl | phenyl |
| Q20 | isopropyl | allyl |
| Q20 | isopropyl | propargyl |
| Q20 | allyl | allyl |
| Q20 | propargyl | propargyl |
| Q21 | methyl | isopropyl |
| Q21 | methyl | cyclopropyl |
| Q21 | methyl | cyclohexyl |
| Q21 | methyl | 1-methyl-2-propenyl |
| Q21 | ethyl | ethyl |
| Q21 | ethyl | isopropyl |
| Q21 | ethyl | cyclopropyl |
| Q21 | ethyl | cyclohexyl |
| Q21 | 2-chloroethyl | isopropyl |
| Q21 | 2-chloroethyl | 2-chloroethyl |
| Q21 | isopropyl | 2,2,2-trifluoroethyl |
| Q21 | n-propyl | isopropyl |
| Q21 | n-propyl | cyclopropyl |
| Q21 | n-propyl | cyclohexyl |
| Q21 | isopropyl | isopropyl |
| Q21 | isopropyl | phenyl |

TABLE 1-continued

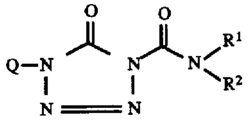

| Q | R¹ | R² |
|---|---|---|
| Q21 | isopropyl | allyl |
| Q21 | isopropyl | propargyl |
| Q21 | allyl | allyl |
| Q21 | propargyl | propargyl |
| Q22 | methyl | isopropyl |
| Q22 | ethyl | ethyl |
| Q22 | ethyl | isopropyl |
| Q22 | n-propyl | isopropyl |
| Q22 | isopropyl | isopropyl |
| Q23 | methyl | n-propyl |
| Q23 | methyl | isopropyl |
| Q23 | methyl | cyclopropyl |
| Q23 | methyl | cyclopentyl |
| Q23 | methyl | cyclohexyl |
| Q23 | methyl | 1-methyl-2-propenyl |
| Q23 | ethyl | ethyl |
| Q23 | ethyl | n-propyl |
| Q23 | ethyl | isopropyl |
| Q23 | ethyl | s-butyl |
| Q23 | ethyl | phenyl |
| Q23 | 2-chloroethyl | isopropyl |
| Q23 | 2-chloroethyl | 2-chloroethyl |
| Q23 | isopropyl | 2,2,2-trifluoroethyl |
| Q23 | n-propyl | isopropyl |
| Q23 | n-propyl | cyclopropyl |
| Q23 | n-propyl | cyclopentyl |
| Q23 | isopropyl | isopropyl |
| Q23 | isopropyl | cyclohexyl |
| Q23 | isopropyl | phenyl |
| Q23 | isopropyl | allyl |
| Q23 | isopropyl | propargyl |
| Q23 | allyl | allyl |
| Q23 | propargyl | propargyl |
| Q24 | methyl | ethyl |
| Q24 | methyl | isopropyl |
| Q24 | methyl | cyclopropyl |
| Q24 | methyl | s-butyl |
| Q24 | methyl | phenyl |
| Q24 | methyl | 1-methyl-2-propenyl |
| Q24 | ethyl | ethyl |
| Q24 | ethyl | isopropyl |
| Q24 | ethyl | cyclopropyl |
| Q24 | ethyl | cyclohexyl |
| Q24 | ethyl | 2,2,2-trifluoroethyl |
| Q24 | n-propyl | 2,2,2-trifluoroethyl |
| Q24 | isopropyl | 2,2,2-trifluoroethyl |
| Q24 | 2-chloroethyl | ethyl |
| Q24 | 2-chloroethyl | n-propyl |
| Q24 | 2-chloroethyl | isopropyl |
| Q24 | 2-chloroethyl | 2-chloroethyl |
| Q24 | n-propyl | isopropyl |
| Q24 | n-propyl | s-butyl |
| Q24 | n-propyl | cyclohexyl |
| Q24 | isopropyl | isopropyl |
| Q24 | isopropyl | cyclohexyl |
| Q24 | isopropyl | phenyl |
| Q24 | isopropyl | allyl |
| Q24 | isopropyl | 2-chloro-2-propenyl |
| Q24 | isopropyl | 2-methyl-2-propenyl |
| Q24 | isopropyl | propargyl |
| Q24 | allyl | allyl |
| Q24 | propargyl | propargyl |
| Q25 | methyl | ethyl |
| Q25 | methyl | isopropyl |
| Q25 | methyl | cyclopropyl |
| Q25 | methyl | cyclohexyl |
| Q25 | methyl | 1-methyl-2-propenyl |
| Q25 | ethyl | ethyl |
| Q25 | ethyl | isopropyl |
| Q25 | ethyl | cyclopropyl |

TABLE 1-continued

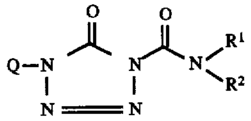

| Q | R¹ | R² |
|---|---|---|
| Q25 | ethyl | cyclohexyl |
| Q25 | 2-chloroethyl | isopropyl |
| Q25 | 2-chloroethyl | 2-chloroethyl |
| Q25 | isopropyl | 2,2,2-trifluoroethyl |
| Q25 | n-propyl | isopropyl |
| Q25 | n-propyl | cyclopropyl |
| Q25 | isopropyl | isopropyl |
| Q25 | isopropyl | phenyl |
| Q25 | isopropyl | allyl |
| Q25 | isopropyl | propargyl |
| Q25 | allyl | allyl |
| Q25 | propargyl | propargyl |
| Q26 | methyl | methyl |
| Q26 | methyl | ethyl |
| Q26 | methyl | n-propyl |
| Q26 | methyl | isopropyl |
| Q26 | methyl | cyclopropyl |
| Q26 | methyl | cyclopentyl |
| Q26 | methyl | cyclohexyl |
| Q26 | methyl | 1-methyl-2-propenyl |
| Q26 | ethyl | ethyl |
| Q26 | ethyl | isopropyl |
| Q26 | ethyl | cyclopropyl |
| Q26 | ethyl | cyclohexyl |
| Q26 | ethyl | 2,2,2-trifluoroethyl |
| Q26 | n-propyl | 2,2,2-trifluoroethyl |
| Q26 | isopropyl | 2,2,2-trifluoroethyl |
| Q26 | 2-chloroethyl | ethyl |
| Q26 | 2-chloroethyl | n-propyl |
| Q26 | 2-chloroethyl | isopropyl |
| Q26 | 2-chloroethyl | 2-chloroethyl |
| Q26 | n-propyl | isopropyl |
| Q26 | n-propyl | cyclopropyl |
| Q26 | isopropyl | isopropyl |
| Q26 | isopropyl | phenyl |
| Q26 | isopropyl | allyl |
| Q26 | isopropyl | 2-chloro-2-propenyl |
| Q26 | isopropyl | 2-methyl-2-propenyl |
| Q26 | isopropyl | propargyl |
| Q26 | allyl | allyl |
| Q26 | propargyl | propargyl |
| Q27 | methyl | isopropyl |
| Q27 | methyl | cyclopropyl |
| Q27 | methyl | cyclohexyl |
| Q27 | ethyl | ethyl |
| Q27 | ethyl | isopropyl |
| Q27 | ethyl | cyclohexyl |
| Q27 | n-propyl | isopropyl |
| Q27 | isopropyl | isopropyl |
| Q27 | isopropyl | phenyl |
| Q28 | ethyl | cyclohexyl |
| Q28 | ethyl | phenyl |
| Q28 | ethyl | 2,2,2-trifluoroethyl |
| Q28 | n-propyl | 2,2,2-trifluoroethyl |
| Q28 | isopropyl | 2,2,2-trifluoroethyl |
| Q28 | 2-chloroethyl | ethyl |
| Q28 | 2-chloroethyl | n-propyl |
| Q28 | 2-chloroethyl | isopropyl |
| Q28 | 2-chloroethyl | 2-chloroethyl |
| Q28 | n-propyl | isopropyl |
| Q28 | n-propyl | cyclopropyl |
| Q28 | n-propyl | s-butyl |
| Q28 | n-propyl | cyclopentyl |
| Q28 | n-propyl | cyclohexyl |
| Q28 | isopropyl | isopropyl |
| Q28 | isopropyl | cyclohexyl |
| Q28 | isopropyl | phenyl |
| Q28 | isopropyl | allyl |
| Q28 | isopropyl | 2-chloro-2-propenyl |
| Q28 | isopropyl | 2-methyl-2-propenyl |

TABLE 1-continued

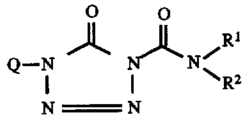

| Q | $R^1$ | $R^2$ |
|---|---|---|
| Q28 | isopropyl | propargyl |
| Q28 | allyl | allyl |
| Q28 | propargyl | propargyl |
| Q29 | methyl | methyl |
| Q29 | methyl | ethyl |
| Q29 | methyl | n-propyl |
| Q29 | methyl | isopropyl |
| Q29 | methyl | cyclopropyl |
| Q29 | methyl | cyclopentyl |
| Q29 | methyl | cyclohexyl |
| Q28 | methyl | phenyl |
| Q28 | methyl | methyl |
| Q28 | methyl | ethyl |
| Q28 | methyl | n-propyl |
| Q28 | methyl | isopropyl |
| Q28 | methyl | cyclopropyl |
| Q28 | methyl | s-butyl |
| Q28 | methyl | cyclopentyl |
| Q28 | methyl | cyclohexyl |
| Q28 | methyl | phenyl |
| Q28 | methyl | 1-methyl-2-propenyl |
| Q28 | ethyl | ethyl |
| Q28 | ethyl | n-propyl |
| Q28 | ethyl | isopropyl |
| Q28 | ethyl | cyclopropyl |
| Q28 | ethyl | s-butyl |
| Q28 | ethyl | cyclopentyl |
| Q29 | methyl | 1-methyl-2-propenyl |
| Q29 | ethyl | ethyl |
| Q29 | ethyl | isopropyl |
| Q29 | ethyl | cyclopropyl |
| Q29 | ethyl | phenyl |
| Q29 | ethyl | 2,2,2-trifluoroethyl |
| Q29 | 2-chloroethyl | ethyl |
| Q29 | 2-chloroethyl | n-propyl |
| Q29 | 2-chloroethyl | isopropyl |
| Q29 | 2-chloroethyl | 2-chloroethyl |
| Q29 | n-propyl | cyclopropyl |
| Q29 | n-propyl | 2,2,2-trifluoroethyl |
| Q29 | isopropyl | 2,2,2-trifluoroethyl |
| Q29 | isopropyl | isopropyl |
| Q29 | isopropyl | phenyl |
| Q29 | isopropyl | allyl |
| Q29 | isopropyl | 2-chloro-2-propenyl |
| Q29 | isopropyl | 2-methyl-2-propenyl |
| Q29 | isopropyl | propargyl |
| Q29 | allyl | allyl |
| Q29 | propargyl | propargyl |
| Q30 | methyl | methyl |
| Q30 | methyl | ethyl |
| Q30 | methyl | n-propyl |
| Q30 | methyl | isopropyl |
| Q30 | methyl | cyclopropyl |
| Q30 | methyl | s-butyl |
| Q30 | methyl | cyclopentyl |
| Q30 | methyl | cyclohexyl |
| Q30 | methyl | phenyl |
| Q30 | methyl | 1-methyl-2-propenyl |
| Q30 | ethyl | ethyl |
| Q30 | ethyl | n-propyl |
| Q30 | ethyl | isopropyl |
| Q30 | ethyl | cyclopropyl |
| Q30 | ethyl | s-butyl |
| Q30 | ethyl | cyclopentyl |
| Q30 | ethyl | cyclohexyl |
| Q30 | ethyl | phenyl |
| Q30 | ethyl | 2,2,2-trifluoroethyl |
| Q30 | n-propyl | 2,2,2-trifluoroethyl |
| Q30 | isopropyl | 2,2,2-trifluoroethyl |
| Q30 | 2-chloroethyl | ethyl |

TABLE 1-continued

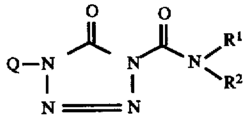

| Q | $R^1$ | $R^2$ |
|---|---|---|
| Q30 | 2-chloroethyl | n-propyl |
| Q30 | 2-chloroethyl | isopropyl |
| Q30 | 2-chloroethyl | 2-chloroethyl |
| Q30 | n-propyl | isopropyl |
| Q30 | n-propyl | cyclopropyl |
| Q30 | n-propyl | s-butyl |
| Q30 | n-propyl | cyclopentyl |
| Q30 | n-propyl | cyclohexyl |
| Q30 | isopropyl | isopropyl |
| Q30 | isopropyl | 2-chloro-2-propenyl |
| Q30 | isopropyl | 2-methyl-2-propenyl |
| Q30 | isopropyl | propargyl |
| Q30 | isopropyl | cyclohexyl |
| Q30 | isopropyl | phenyl |
| Q30 | isopropyl | allyl |
| Q30 | allyl | allyl |
| Q30 | propargyl | propargyl |
| Q31 | methyl | ethyl |
| Q31 | methyl | n-propyl |
| Q31 | methyl | isopropyl |
| Q31 | methyl | cyclopropyl |
| Q31 | methyl | s-butyl |
| Q31 | methyl | 1-methyl-2-propenyl |
| Q31 | ethyl | ethyl |
| Q31 | ethyl | n-propyl |
| Q31 | ethyl | isopropyl |
| Q31 | ethyl | cyclopropyl |
| Q31 | ethyl | 2,2,2-trifluoroethyl |
| Q31 | n-propyl | 2,2,2-trifluoroethyl |
| Q31 | isopropyl | 2,2,2-trifluoroethyl |
| Q31 | 2-chloroethyl | ethyl |
| Q31 | 2-chloroethyl | n-propyl |
| Q31 | 2-chloroethyl | isopropyl |
| Q31 | 2-chloroethyl | 2-chloroethyl |
| Q31 | n-propyl | isopropyl |
| Q31 | n-propyl | cyclopropyl |
| Q31 | isopropyl | isopropyl |
| Q31 | isopropyl | phenyl |
| Q31 | isopropyl | allyl |
| Q31 | isopropyl | 2-chloro-2-propenyl |
| Q31 | isopropyl | 2-methyl-2-propenyl |
| Q31 | isopropyl | propargyl |
| Q31 | allyl | allyl |
| Q31 | propargyl | propargyl |
| Q32 | methyl | ethyl |
| Q32 | methyl | n-propyl |
| Q32 | methyl | isopropyl |
| Q32 | methyl | cyclopropyl |
| Q32 | methyl | s-butyl |
| Q32 | methyl | cyclopentyl |
| Q32 | methyl | cyclohexyl |
| Q32 | methyl | phenyl |
| Q32 | methyl | 1-methyl-2-propenyl |
| Q32 | ethyl | ethyl |
| Q32 | ethyl | n-propyl |
| Q32 | ethyl | isopropyl |
| Q32 | ethyl | cyclopropyl |
| Q32 | ethyl | s-butyl |
| Q32 | ethyl | cyclopentyl |
| Q32 | ethyl | cyclohexyl |
| Q32 | ethyl | phenyl |
| Q32 | n-propyl | isopropyl |
| Q32 | n-propyl | cyclopropyl |
| Q32 | n-propyl | s-butyl |
| Q32 | n-propyl | cyclopentyl |
| Q32 | n-propyl | cyclohexyl |
| Q32 | isopropyl | isopropyl |
| Q32 | isopropyl | cyclohexyl |
| Q32 | isopropyl | phenyl |
| Q32 | isopropyl | allyl |

TABLE 1-continued

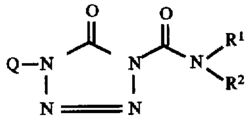

| Q | R¹ | R² |
|---|---|---|
| Q32 | isopropyl | 2-chloro-2-propenyl |
| Q32 | isopropyl | 2-methyl-2-propenyl |
| Q32 | isopropyl | propargyl |
| Q32 | allyl | allyl |
| Q32 | propargyl | propargyl |
| Q33 | methyl | methyl |
| Q33 | methyl | ethyl |
| Q33 | methyl | n-propyl |
| Q33 | methyl | isopropyl |
| Q33 | methyl | cyclopropyl |
| Q33 | methyl | s-butyl |
| Q33 | methyl | cyclopentyl |
| Q33 | methyl | cyclohexyl |
| Q33 | methyl | phenyl |
| Q33 | methyl | 1-methyl-2-propenyl |
| Q33 | ethyl | ethyl |
| Q33 | ethyl | n-propyl |
| Q33 | ethyl | isopropyl |
| Q33 | ethyl | cyclopropyl |
| Q33 | ethyl | s-butyl |
| Q33 | ethyl | cyclopentyl |
| Q33 | ethyl | cyclohexyl |
| Q33 | ethyl | phenyl |
| Q33 | ethyl | 2,2,2-trifluoroethyl |
| Q33 | n-propyl | 2,2,2-trifluoroethyl |
| Q33 | isopropyl | 2,2,2-trifluoroethyl |
| Q33 | 2-chloroethyl | ethyl |
| Q33 | 2-chloroethyl | n-propyl |
| Q33 | 2-chloroethyl | isopropyl |
| Q33 | 2-chloroethyl | 2-chloroethyl |
| Q33 | n-propyl | isopropyl |
| Q33 | n-propyl | cyclopropyl |
| Q33 | n-propyl | s-butyl |
| Q33 | n-propyl | cyclopentyl |
| Q33 | n-propyl | cyclohexyl |
| Q33 | isopropyl | isopropyl |
| Q33 | isopropyl | cyclohexyl |
| Q33 | isopropyl | phenyl |
| Q33 | isopropyl | allyl |
| Q33 | isopropyl | propargyl |
| Q33 | allyl | allyl |
| Q33 | propargyl | propargyl |
| Q34 | methyl | n-propyl |
| Q34 | methyl | isopropyl |
| Q34 | methyl | cyclopropyl |
| Q34 | methyl | cyclopentyl |
| Q34 | methyl | cyclohexyl |
| Q34 | methyl | 1-methyl-2-propenyl |
| Q34 | ethyl | ethyl |
| Q34 | ethyl | isopropyl |
| Q34 | ethyl | cyclopropyl |
| Q34 | ethyl | cyclopentyl |
| Q34 | ethyl | cyclohexyl |
| Q34 | ethyl | 2,2,2-trifluoroethyl |
| Q34 | n-propyl | 2,2,2-trifluoroethyl |
| Q34 | isopropyl | 2,2,2-trifluoroethyl |
| Q34 | 2-chloroethyl | ethyl |
| Q34 | 2-chloroethyl | n-propyl |
| Q34 | 2-chloroethyl | isopropyl |
| Q34 | 2-chloroethyl | 2-chloroethyl |
| Q34 | n-propyl | isopropyl |
| Q34 | n-propyl | cyclopropyl |
| Q34 | n-propyl | cyclohexyl |
| Q34 | isopropyl | isopropyl |
| Q34 | isopropyl | cyclohexyl |
| Q34 | isopropyl | phenyl |
| Q34 | isopropyl | allyl |
| Q34 | isopropyl | 2-chloro-2-propenyl |
| Q34 | isopropyl | 2-methyl-2-propenyl |
| Q34 | isopropyl | propargyl |

TABLE 1-continued

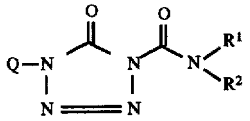

| Q | R¹ | R² |
|---|---|---|
| Q34 | allyl | allyl |
| Q34 | propargyl | propargyl |
| Q35 | methyl | n-propyl |
| Q35 | methyl | isopropyl |
| Q35 | methyl | cyclopropyl |
| Q35 | methyl | s-butyl |
| Q35 | methyl | cyclopentyl |
| Q35 | methyl | cyclohexyl |
| Q35 | methyl | 1-methyl-2-propenyl |
| Q35 | ethyl | ethyl |
| Q35 | ethyl | isopropyl |
| Q35 | ethyl | cyclopropyl |
| Q35 | ethyl | cyclopentyl |
| Q35 | ethyl | cyclohexyl |
| Q35 | ethyl | 2,2,2-trifluoroethyl |
| Q35 | n-propyl | 2,2,2-trifluoroethyl |
| Q35 | isopropyl | 2,2,2-trifluoroethyl |
| Q35 | 2-chloroethyl | ethyl |
| Q35 | 2-chloroethyl | n-propyl |
| Q35 | 2-chloroethyl | isopropyl |
| Q35 | 2-chloroethyl | 2-chloroethyl |
| Q35 | n-propyl | isopropyl |
| Q35 | n-propyl | cyclopropyl |
| Q35 | n-propyl | cyclohexyl |
| Q35 | isopropyl | isopropyl |
| Q35 | isopropyl | cyclohexyl |
| Q35 | isopropyl | phenyl |
| Q35 | isopropyl | allyl |
| Q35 | isopropyl | 2-chloro-2-propenyl |
| Q35 | isopropyl | 2-methyl-2-propenyl |
| Q35 | isopropyl | propargyl |
| Q35 | allyl | allyl |
| Q35 | propargyl | propargyl |
| Q36 | methyl | methyl |
| Q36 | methyl | ethyl |
| Q36 | methyl | n-propyl |
| Q36 | methyl | isopropyl |
| Q36 | methyl | cyclopropyl |
| Q36 | methyl | s-butyl |
| Q36 | methyl | cyclopentyl |
| Q36 | methyl | cyclohexyl |
| Q36 | methyl | phenyl |
| Q36 | methyl | 1-methyl-2-propenyl |
| Q36 | ethyl | ethyl |
| Q36 | ethyl | n-propyl |
| Q36 | ethyl | isopropyl |
| Q36 | ethyl | cyclopropyl |
| Q36 | ethyl | s-butyl |
| Q36 | ethyl | cyclopentyl |
| Q36 | ethyl | cyclohexyl |
| Q36 | ethyl | phenyl |
| Q36 | ethyl | 2,2,2-trifluoroethyl |
| Q36 | n-propyl | 2,2,2-trifluoroethyl |
| Q36 | isopropyl | 2,2,2-trifluoroethyl |
| Q36 | 2-chloroethyl | ethyl |
| Q36 | 2-chloroethyl | n-propyl |
| Q36 | 2-chloroethyl | isopropyl |
| Q36 | 2-chloroethyl | 2-chloroethyl |
| Q36 | n-propyl | isopropyl |
| Q36 | n-propyl | cyclopropyl |
| Q36 | n-propyl | s-butyl |
| Q36 | n-propyl | cyclopentyl |
| Q36 | n-propyl | cyclohexyl |
| Q36 | isopropyl | isopropyl |
| Q36 | isopropyl | cyclohexyl |
| Q36 | isopropyl | phenyl |
| Q36 | isopropyl | allyl |
| Q36 | isopropyl | 2-chloro-2-propenyl |
| Q36 | isopropyl | 2-chloro-2-propenyl |
| Q36 | isopropyl | propargyl |

TABLE 1-continued

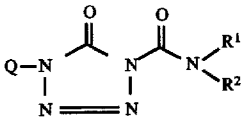

| Q | R¹ | R² |
|---|---|---|
| Q36 | allyl | allyl |
| Q36 | propargyl | propargyl |
| Q37 | methyl | methyl |
| Q37 | methyl | ethyl |
| Q37 | methyl | n-propyl |
| Q37 | methyl | isopropyl |
| Q37 | methyl | cyclopropyl |
| Q37 | methyl | s-butyl |
| Q37 | methyl | cyclopentyl |
| Q37 | methyl | cyclohexyl |
| Q37 | methyl | phenyl |
| Q37 | methyl | 1-methyl-2-propenyl |
| Q37 | ethyl | ethyl |
| Q37 | ethyl | n-propyl |
| Q37 | ethyl | isopropyl |
| Q37 | ethyl | cyclopropyl |
| Q37 | ethyl | s-butyl |
| Q37 | ethyl | cyclopentyl |
| Q37 | ethyl | cyclohexyl |
| Q37 | ethyl | phenyl |
| Q37 | ethyl | 2,2,2-trifluoroethyl |
| Q37 | n-propyl | 2,2,2-trifluoroethyl |
| Q37 | isopropyl | 2,2,2-trifluoroethyl |
| Q37 | 2-chloroethyl | ethyl |
| Q37 | 2-chloroethyl | n-propyl |
| Q37 | 2-chloroethyl | isopropyl |
| Q37 | 2-chloroethyl | 2-chloroethyl |
| Q37 | n-propyl | isopropyl |
| Q37 | n-propyl | cyclopropyl |
| Q37 | n-propyl | s-butyl |
| Q37 | n-propyl | cyclopentyl |
| Q37 | n-propyl | cyclohexyl |
| Q37 | isopropyl | isopropyl |
| Q37 | isopropyl | cyclohexyl |
| Q37 | isopropyl | phenyl |
| Q37 | isopropyl | allyl |
| Q37 | isopropyl | 2-chloro-2-propenyl |
| Q37 | isopropyl | 2-methyl-2-propenyl |
| Q37 | isopropyl | propargyl |
| Q37 | allyl | allyl |
| Q37 | propargyl | propargyl |
| Q38 | methyl | methyl |
| Q38 | methyl | ethyl |
| Q38 | methyl | n-propyl |
| Q38 | methyl | isopropyl |
| Q38 | methyl | cyclopropyl |
| Q38 | methyl | s-butyl |
| Q38 | methyl | cyclopentyl |
| Q38 | methyl | cyclohexyl |
| Q38 | methyl | phenyl |
| Q38 | methyl | 1-methyl-2-propenyl |
| Q38 | ethyl | ethyl |
| Q38 | ethyl | n-propyl |
| Q38 | ethyl | isopropyl |
| Q38 | ethyl | cyclopropyl |
| Q38 | ethyl | s-butyl |
| Q38 | ethyl | cyclopentyl |
| Q38 | ethyl | cyclohexyl |
| Q38 | ethyl | phenyl |
| Q38 | ethyl | 2,2,2-trifluoroethyl |
| Q38 | n-propyl | 2,2,2-trifluoroethyl |
| Q38 | isopropyl | 2,2,2-trifluoroethyl |
| Q38 | 2-chloroethyl | ethyl |
| Q38 | 2-chloroethyl | n-propyl |
| Q38 | 2-chloroethyl | isopropyl |
| Q38 | 2-chloroethyl | 2-chloroethyl |
| Q38 | n-propyl | isopropyl |
| Q38 | n-propyl | cyclopropyl |
| Q38 | n-propyl | s-butyl |
| Q38 | n-propyl | cyclopentyl |

TABLE 1-continued

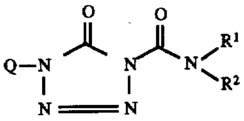

| Q | R¹ | R² |
|---|---|---|
| Q38 | n-propyl | cyclohexyl |
| Q38 | isopropyl | isopropyl |
| Q38 | isopropyl | cyclohexyl |
| Q38 | isopropyl | phenyl |
| Q38 | isopropyl | allyl |
| Q38 | isopropyl | 2-chloro-2-propenyl |
| Q38 | isopropyl | 2-methyl-2-propenyl |
| Q38 | isopropyl | propargyl |
| Q38 | allyl | allyl |
| Q38 | propargyl | propargyl |
| Q39 | methyl | isopropyl |
| Q39 | methyl | cyclopropyl |
| Q39 | ethyl | ethyl |
| Q39 | ethyl | isopropyl |
| Q39 | ethyl | cyclopropyl |
| Q39 | n-propyl | isopropyl |
| Q39 | isopropyl | isopropyl |
| Q39 | isopropyl | phenyl |
| Q40 | methyl | ethyl |
| Q40 | methyl | isopropyl |
| Q40 | methyl | cyclopropyl |
| Q40 | methyl | 1-methyl-2-propenyl |
| Q40 | ethyl | ethyl |
| Q40 | ethyl | isopropyl |
| Q40 | ethyl | cyclopropyl |
| Q40 | ethyl | cyclohexyl |
| Q40 | n-propyl | isopropyl |
| Q40 | n-propyl | cyclopropyl |
| Q40 | n-propyl | cyclohexyl |
| Q40 | isopropyl | isopropyl |
| Q40 | isopropyl | phenyl |
| Q40 | isopropyl | allyl |
| Q41 | methyl | methyl |
| Q41 | methyl | ethyl |
| Q41 | methyl | n-propyl |
| Q41 | methyl | isopropyl |
| Q41 | methyl | cyclopropyl |
| Q41 | methyl | s-butyl |
| Q41 | methyl | cyclopentyl |
| Q41 | methyl | cyclohexyl |
| Q41 | methyl | phenyl |
| Q41 | methyl | 1-methyl-2-propenyl |
| Q41 | ethyl | ethyl |
| Q41 | ethyl | n-propyl |
| Q41 | ethyl | isopropyl |
| Q41 | ethyl | cyclopropyl |
| Q41 | ethyl | s-butyl |
| Q41 | ethyl | cyclopentyl |
| Q41 | ethyl | cyclohexyl |
| Q41 | ethyl | phenyl |
| Q41 | n-propyl | isopropyl |
| Q41 | n-propyl | cyclopropyl |
| Q41 | n-propyl | s-butyl |
| Q41 | n-propyl | cyclopentyl |
| Q41 | n-propyl | cyclohexyl |
| Q41 | isopropyl | isopropyl |
| Q41 | isopropyl | cyclohexyl |
| Q41 | isopropyl | phenyl |
| Q41 | isopropyl | allyl |
| Q41 | isopropyl | 2-chloro-2-propenyl |
| Q41 | isopropyl | 2-methyl-2-propenyl |
| Q41 | isopropyl | propargyl |
| Q41 | allyl | allyl |
| Q41 | propargyl | propargyl |

TABLE 2

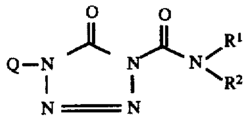

| Q | 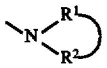 |
|---|---|
| Q1 | pyrrolidinyl |
| Q1 | piperidyl |
| Q2 | piperidyl |
| Q2 | morpholinyl |
| Q3 | pyrrolidinyl |
| Q3 | morpholinyl |
| Q4 | pyrrolidinyl |
| Q4 | piperidyl |
| Q4 | morpholinyl |
| Q4 | 2-methylpiperidyl |
| Q5 | pyrrolidinyl |
| Q5 | piperidyl |
| Q5 | morpholinyl |
| Q5 | 2-methyl-1,2,3,4-tetrahydroquinolyl |
| Q5 | 2,5-dimethylpyrrolidinyl |
| Q5 | 2,5-dimethyl-3-pyrrolinyl |
| Q5 | 2,6-dimethylpiperidyl |
| Q6 | pyrrolidinyl |
| Q6 | piperidyl |
| Q6 | morpholinyl |
| Q6 | 2,5-dimethylpyrrolidinyl |
| Q7 | pyrrolidinyl |
| Q7 | piperidyl |
| Q7 | morpholinyl |
| Q8 | pyrrolidinyl |
| Q8 | piperidyl |
| Q8 | morpholinyl |
| Q8 | 2-methylpiperidyl |
| Q8 | 2,5-dimethylpyrrolidinyl |
| Q8 | 2,5-dimethyl-3-pyrrolinyl |
| Q8 | 2,6-dimethylpiperidyl |
| Q9 | pyrrolidinyl |
| Q9 | piperidyl |
| Q9 | morpholinyl |
| Q9 | 2,6-dimethylpiperidyl |
| Q10 | pyrrolidinyl |
| Q10 | piperidyl |
| Q10 | morpholinyl |
| Q11 | pyrrolidinyl |
| Q11 | piperidyl |
| Q11 | morpholinyl |
| Q12 | pyrrolidinyl |
| Q12 | piperidyl |
| Q12 | morpholinyl |
| Q13 | pyrrolidinyl |
| Q13 | piperidyl |
| Q13 | morpholinyl |
| Q14 | pyrrolidinyl |
| Q14 | piperidyl |
| Q14 | morpholinyl |
| Q14 | 2-methylpiperidyl |
| Q14 | 2,5-dimethylpyrrolidinyl |
| Q14 | 2,5-dimethyl-3-pyrrolinyl |
| Q14 | 2,6-dimethylpiperidyl |
| Q15 | pyrrolidinyl |
| Q15 | piperidyl |
| Q15 | morpholinyl |
| Q15 | 2,6-dimethylpiperidyl |
| Q16 | pyrrolidinyl |
| Q16 | piperidyl |
| Q16 | morpholinyl |
| Q17 | pyrrolidinyl |
| Q17 | piperidyl |
| Q17 | morpholinyl |
| Q18 | pyrrolidinyl |
| Q18 | piperidyl |
| Q18 | morpholinyl |
| Q18 | 2,6-dimethylpiperidyl |

TABLE 2-continued

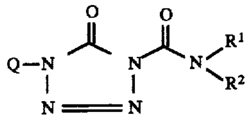

| Q | 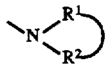 |
|---|---|
| Q19 | pyrrolidinyl |
| Q19 | piperidyl |
| Q19 | morpholinyl |
| Q19 | 2,5-dimethylpyrrolidinyl |
| Q19 | 2,5-dimethyl-3-pyrrolinyl |
| Q19 | 2,6-dimethylpiperidyl |
| Q20 | pyrrolidinyl |
| Q20 | piperidyl |
| Q20 | morpholinyl |
| Q20 | 2-methyl-1,2,3,4-tetrahydroquinolyl |
| Q21 | pyrrolidinyl |
| Q21 | piperidyl |
| Q21 | morpholinyl |
| Q21 | 2-methylpiperidyl |
| Q22 | pyrrolidinyl |
| Q22 | piperidyl |
| Q23 | pyrrolidinyl |
| Q23 | piperidyl |
| Q23 | morpholinyl |
| Q23 | 2,5-dimethylpyrrolidinyl |
| Q23 | 2,6-dimethylpiperidyl |
| Q24 | pyrrolidinyl |
| Q24 | piperidyl |
| Q24 | morpholinyl |
| Q24 | 2-methylpiperidyl |
| Q24 | 2,5-dimethylpyrrolidinyl |
| Q24 | 2,5-dimethyl-3-pyrrolinyl |
| Q24 | 2,6-dimethylpiperidyl |
| Q25 | pyrrolidinyl |
| Q25 | piperidyl |
| Q25 | morpholinyl |
| Q25 | 2,5-dimethylpyrrolidinyl |
| Q25 | 2,6-dimethylpiperidyl |
| Q26 | pyrrolidinyl |
| Q26 | piperidyl |
| Q26 | morpholinyl |
| Q26 | 2,5-dimethylpyrrolidinyl |
| Q26 | 2,6-dimethylpiperidyl |
| Q26 | 2,5-dimethyl-3-pyrrolinyl |
| Q27 | pyrrolidinyl |
| Q27 | piperidyl |
| Q28 | pyrrolidinyl |
| Q28 | piperidyl |
| Q28 | morpholinyl |
| Q28 | 2-methylpiperidyl |
| Q28 | 2,5-dimethylpyrrolidinyl |
| Q28 | 2,6-dimethylpiperidyl |
| Q28 | 2-methyl-1,2,3,4-tetrahydroquinolyl |
| Q28 | 2,5-dimethyl-3-pyrrolinyl |
| Q29 | pyrrolidinyl |
| Q29 | piperidyl |
| Q29 | morpholinyl |
| Q29 | 2,5-dimethylpyrrolidinyl |
| Q29 | 2,5-dimethyl-3-pyrrolinyl |
| Q29 | 2,6-dimethylpiperidyl |
| Q30 | pyrrolidinyl |
| Q30 | piperidyl |
| Q30 | morpholinyl |
| Q30 | 2-methylpiperidyl |
| Q30 | 2,5-dimethylpyrrolidinyl |
| Q30 | 2,5-dimethyl-3-pyrrolinyl |
| Q30 | 2,6-dimethylpiperidyl |
| Q30 | 2-methyl-1,2,3,4-tetrahydroquinolyl |
| Q31 | pyrrolidinyl |
| Q31 | piperidyl |
| Q31 | morpholinyl |
| Q32 | pyrrolidinyl |
| Q32 | piperidyl |

TABLE 2-continued

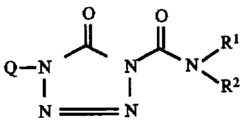

| Q | 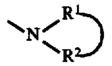 |
|---|---|
| Q32 | morpholinyl |
| Q32 | 2-methylpiperidyl |
| Q32 | 2,5-dimethylpyrrolidinyl |
| Q32 | 2,6-dimethylpiperidyl |
| Q32 | 2-methyl-1,2,3,4-tetrahydroquinolyl |
| Q33 | pyrrolidinyl |
| Q33 | piperidyl |
| Q33 | 2,6-dimethylpiperidyl |
| Q33 | morpholinyl |
| Q33 | 2-methylpiperidyl |
| Q33 | 2,5-dimethylpyrrolidinyl |
| Q33 | 2,6-dimethylpiperidyl |
| Q33 | 2-methyl-1,2,3,4-tetrahydroquinolyl |
| Q34 | pyrrolidinyl |
| Q34 | piperidyl |
| Q34 | morpholinyl |
| Q34 | 2,5-dimethylpyrrolidinyl |
| Q34 | 2,5-dimethyl-3-pyrrolinyl |
| Q34 | 2,6-dimethylpiperidyl |
| Q35 | pyrrolidinyl |
| Q35 | piperidyl |
| Q35 | morpholinyl |
| Q35 | 2,5-dimethylpyrrolidinyl |
| Q35 | 2,5-dimethyl-3-pyrrolinyl |
| Q35 | 2,6-dimethylpiperidyl |
| Q36 | pyrrolidinyl |
| Q36 | piperidyl |
| Q36 | morpholinyl |
| Q36 | 2-methylpiperidyl |
| Q36 | 2,5-dimethylpyrrolidinyl |
| Q36 | 2,5-dimethyl-3-pyrrolinyl |
| Q36 | 2,6-dimethylpiperidyl |
| Q36 | 2-methyl-1,2,3,4-tetrahydroquinolyl |
| Q37 | pyrrolidinyl |
| Q37 | piperidyl |
| Q37 | morpholinyl |
| Q37 | 2-methylpiperidyl |
| Q37 | 2,5-dimethyl-3-pyrrolinyl |
| Q37 | 2,5-dimethylpyrrolidinyl |
| Q37 | 2,6-dimethylpiperidyl |
| Q37 | 2-methyl-1,2,3,4-tetrahydroquinolyl |
| Q38 | pyrrolidinyl |
| Q38 | piperidyl |
| Q38 | morpholinyl |
| Q38 | 2,6-dimethylpiperidyl |
| Q38 | 2-methylpiperidyl |
| Q38 | 2,5-dimethylpyrrolidinyl |
| Q38 | 2,5-dimethyl-3-pyrrolinyl |
| Q38 | 2-methyl-1,2,3,4-tetrahydroquinolyl |
| Q39 | pyrrolidinyl |
| Q39 | piperidyl |
| Q39 | morpholinyl |
| Q40 | pyrrolidinyl |
| Q40 | piperidyl |
| Q40 | morpholinyl |
| Q40 | 2-methyl-1,2,3,4-tetrahydroquinolyl |
| Q41 | pyrrolidinyl |
| Q41 | piperidyl |
| Q41 | morpholinyl |
| Q41 | 2,5-dimethylpyrrolidinyl |

When in the process (a), for example, 1-(2-chloro-3-pyridyl)-5(4H)-tetrazolinone and diethylcarbamoyl chloride are used as starting materials, the course of the reaction can be represented by the following equation:

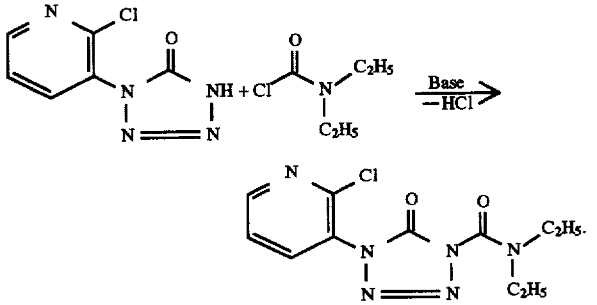

In the process (a), the starting materials of the formula (II) mean those based on the above definition of $R^3$ and n, and preferably those based on the above preferred definitions.

The compounds of the formula (II) are novel, and can be obtained when (b) compounds of the formula (IV)

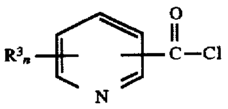

(IV)

wherein $R^3$ and n have the stone meanings as mentioned above, are reacted with trimethylsilylazide (at least 2 mols) and then with water or—preferably—with methanol, or (c) compounds of the formula (V)

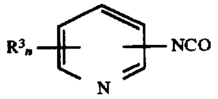

(V)

wherein $R^3$ and n have the stone meanings as mentioned above, are reacted first with trimethylsilylazide and then with water or—preferably—with methanol, or (d) compounds of the formula (VI)

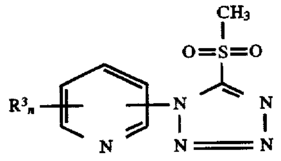

(VI)

wherein $R^3$ and n have the stone meanings as mentioned above, are reacted with an inorganic base (optionally in aqueous solution), in the presence of inert solvents, and if appropriate, in the presence of acid binders, or (e) compounds of the formula (VII)

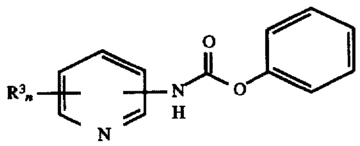

(VII)

wherein $R^3$ and n have the stone meanings as mentioned above, are reacted with sodium azide, in the presence of anhydrous aluminum chloride and in the presence of inert solvents.

The compounds of the formula (IV) are well known compounds in the field of organic chemistry (being sold generally as a reagent). The following compounds, are illustrative:

picolinic acid chloride,
nicotinic acid chloride,
isonicotinic acid chloride,
2-methylthio nicotinic acid chloride, and
2,6-dichloroisonicotinic acid chloride.

The compounds of the formula (IV) can easily be obtained by chlorinating, in a usual manner, the compounds represented by the formula (VIII)

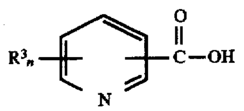

(VIII)

wherein $R^3$ and n have the same meanings as mentioned above.

The preferred compounds of the formula (VIII) are those wherein $R^3$ and n have the preferred definitions set forth hereinabove.

The compounds of the formula (VIII) are well known compounds in the field of organic chemistry. For example, said compounds may be synthesized by the processes described in WO 93/8005, French Patent Laid-Open 2686340, EP-A 166907, 181311, 55011, Japanese Patent Laid-Open Application Hei 3-81263, Journal of the Chemical Society of London, vol. 67, page 407, vol. 73, page 590, Journal of Organic Chemistry, vol. 19, page 633, 1954, Tetrahedron, vol. 50(No. 4), pages 1129–1134, 1994, Bulletin de la Societe Chimiqque de France, (3–4, Pt.2), pages 530–532, 1976, Applied Radiation. Isotopes, vol. 2 (No. 3), pages 215–220, 1991, Chemisch Berichte, vol. 14, page 645, 1881, vol. 19, page 1305, 1886, vol. 35, page 1352, 1902, vol. 61, page 2202, 1928, Journal of Chemical Research, Synopsis, (1), pages 20–21, 1986, Journal of Pharmacie de Belgique,vol. 35 (No. 2), pages 98–102, 1980, or by processes similar thereto, some sold as reagents. The following compounds, for example, are illustrative:

| | |
|---|---|
| picolinic acid, | nicotinic acid, |
| isonicotinic acid, | 2-chloronicotinic acid, |
| 6-chloronicotinic acid, | 2-methylnicotinic acid, |
| 2-methoxynicotinic acid, | 4-trifluoromethylnicotinic acid, |
| 2,6-dichloronicotinic acid, | 2-chloro-6-methylnicotinic acid, |
| 4-fluoronicotinic acid, | 4-chloronicotinic acid, |
| 3-fluoroisonicotinic acid, | 3-bromoisonicotinic acid, |
| 2-chloroisonicotinic acid, | 3-chloroisonicitinic acid, |
| 4-methylnicotinic acid, | 3-methylisonicotinic acid, |
| 3-methylthioisonicotinic acid, | 2-trifluoromethylnicotinic acid, |
| 3,5-dichloroisonicotinic acid, | 2-chloro-4-methylnicoticic acid, |
| 2,6-dimethylnicoticinic acid, | 2,4-dimethylnicotinic acid, |
| 4-ethylnicotinic acid, | 2-methylthionicotinic acid, |
| 5-trifluoromethoxypicolicinc acid, | 2-chloro-4,6-dimethylnicotinic acid, |
| 6-chloro-2,4-dimethylnicotinic acid, | 5-tricluoromethoxypicolinic acid, |
| 4,6-dimethoxy-2-trifluoromethyl-nicotinic acid. | and |

The reaction of the above-mentioned process (b) can be carried out in a similar manner to the synthesis of tetrazolinones described in Journal of Chemical Society, Perkin Transaction 1, 1992, pages 1101–1104, or The Journal of American Chemical Society, Vol. 81, 1959, pages 3076–3079.

In the process,(c) according to the invention, the preferred starting compounds of the formula (V) are those based on the above preferred definition of $R^1$ and n.

The compounds of the formula (V) are well known compounds in the field of organic chemistry, for example, 2,6-dichloro-4-pyridyl isocyanate. Said compounds can also easily be obtained by Curtius rearrangement of the compounds of the above mentioned formula (IV) or by Schmidt rearrangement of compounds of the above-mentioned formula (VIII).

The reaction of the above-mentioned process (c) can be carried out in a similar manner to the synthesis of tetrazolinones described in The Journal of Organic Chemistry, Vol. 45, 1980, pages 5130–5136 or The Journal of American Chemical Society, vol. 81, 1959, pages 3076–3079.

In the above-mentioned process (d), preferred starting compounds of the formula (VI) are those based on the above preferred definitions of $R^1$ and n.

The compounds of the formula (VI) can easily be prepared by the following process (f):

(f) compounds of the following formula (IX)

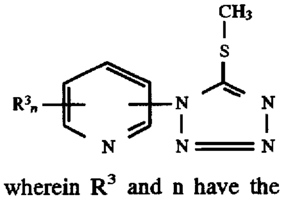

(IX)

wherein $R^3$ and n have the same meanings as mentioned above are reacted with oxidizing agents, in the presence of inert solvents.

In the above-mentioned process (f), the preferred starting compounds of the formula (IX) are those base on the above preferred definitions of $R^1$ and n.

In the above-mentioned process (f), the oxidizing agents preferably have a suitable oxidative effect such that one nitrogen atom of the pyridine ring is not oxidized. As examples of said oxidizing agent, there may be mentioned: OXONE® potassium permanganate, potassium hydrogen persulfate, ruthenium oxide, osmium oxide, sodium metaperiodate, dinitrogen tetroxide, hydrogen peroxide, peracid, hydroperoxide and ozone. When hydrogen peroxide is used as oxidizing agent, it is advantageous to use a tungsten catalyst such as sodium tungstate.

The compounds of the formula (IX) can easily be prepared by the following process (g):

(g) compounds of the following formula (X)

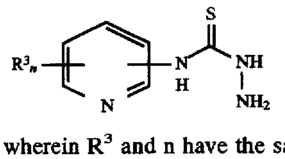

(X)

wherein $R^3$ and n have the same meanings mentioned above, are reacted with dimethyl sulfate and then, under acid conditions, the resulting products are reacted with sodium nitrite or potassium nitrite.

The reaction of the process (E) can be carried out in a manner similar to the synthesis of tetrazolinones described in Chemische Berichte vol. 34, page 3115, 1901.

In the above-mentioned process (g), the preferred starting compounds of, the formula (X) are those based on the above preferred definitions of $R^1$ and n.

The compounds of the formula (X) can be obtained by the following known process (h):

(h) compounds of the following formula (XI)

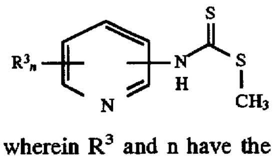

(XI)

wherein $R^3$ and n have the same meaning mentioned above, are reacted with hydrazine.

In the reaction of the process (h), the preferred starting compounds of the formula (XI) are those based on the above preferred definitions of $R^1$ and n.

The compounds of the formula (XI) can be obtained by the following process (i):

(i) compounds of the following formula (XII)

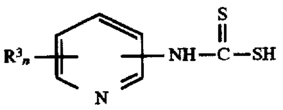

(XII)

wherein $R^3$ and n have the same meanings mentioned above, are reacted with methyliodide.

In the reaction of the process (i), the starting compounds of the formula (XII) mean those based on the above definitions of $R^3$ and n, and preferably based on the above preferred definitions.

The compounds of the formula (XII) can be obtained by the following process (j):

(j) aminopyridines of the following formula (XIII)

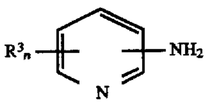

(XIII)

wherein $R^3$ and n have the same meanings mentioned above, are reacted with carbon disulfide, in the presence of tertiary amines such as triethyl amine, and if appropriate in the presence of inert solvents.

In the reaction of the process (j), the starting compounds of the formula (XIII) mean those based on the above definitions of $R^3$ and n, and preferably based on the above preferred definitions.

In the reactions of the processes (i) and (j) can be carried out in a similar manner to the method of preparing tetrazolinones described in Journal of the Chemical Society, pages 796–802, 1955 or pages 1644–1649,1956. The compounds of the formula (XIII) are well known compounds in the field of organic chemistry. For example, said compounds may be synthesized by the processes described in Recueil des Travaux Chimiques des Pays. Bas, vol. 69, pages 673, 1950, The Journal of American Chemical Society, vol. 69, page 63, 1947, vol. 69, page 69, 1947, vol. 73 pages 5043–5046, 1951, The Journal of Organic Chemistry, vol. 19, page 1633, 1954 or by processes similar thereto, or are commercially available. As examples of said compounds, there my be mentioned:

| | |
|---|---|
| 2-aminopyridine, | 3-aminopyridine, |
| 4-aminopyridine, | 2-amino-3-chloropyridine, |
| 2-amino-3-methylpyridine, | 3-amino-2-methylpyridine, |
| 4-amino-3-methylpyridine, | 2-amino-3-methoxypyridine, |
| 2-amino-3,5-dichloropyridine, | 4-amino-2,6-dichloropyridine, and |
| 2-amino-3-chloro-5-trifluoro-methylpyridine. | |

The compounds of the formula (XIII) can be obtained by the following known process (k):

(k) chloropyridines of the formula (XIV)

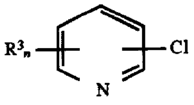

(XIV)

wherein $R^3$ and n have the same meanings mentioned above, are aminated.

The above-mentioned process (k) can be carried out similarly to that described in, for example, Heterocycles vol. 26, pages 2065–2068, 1987, Vol. 22, pages 117–124, 1984, or Japanese Patent Laid-Open Application Sho 62-155260.

In the reaction of the process (k), the starting compounds of the formula (XIV) mean those based on the above definitions of $R^3$ and n, and preferably based on the above preferred definitions.

Chloropyridines represented by the formula (XIV) are well known compounds in the field of organic chemistry being sold as reagents, and for example there may be mentioned:

2-chloro-3-trifluoromethylpyridine, 2-chloro-5-trifluoromethylpyridine, and 2-chloro-3,5-ditrifluoromethylpyridine.

In the process (d), as examples of the inorganic bases, there may be mentioned:

| | |
|---|---|
| sodium hydroxide, | potassium hydroxide, |
| sodium carbonate, | potassium carbonate, |
| sodium bicarbonate, and | potassium bicarbonate. |

In the reaction of the process (e), the starting compounds of the formula (VII) mean those based on the above definitions of $R^3$ and n, and preferably based on the above preferred definitions.

The compounds of the formula (VII) can easily be obtained by the following known process (l):

(l) aminopyridines represented by the above-mentioned formula (XIII) are reacted with phenylchloroformate, if appropriate in the presence of inert solvents.

In carrying out the process (e) mentioned above, use may be made, as suitable diluent, of any inert solvent.

Examples of such diluents are aliphatic, cycloaliphatic and aromatic, optionally chlorinated, hydrocarbons such as toluene, xylene, chlorobenzene, dichlorobenzene, and the like; ethers such as ethyl ether, methyl ethyl ether, isopropyl ether, butyl ether, dioxane, dimethoxyethane (DME), tetrahydrofurane (THF) dimethylene glycol, dimethyl ether (DGM) and the like; acid amides such as dimethyl formamide (DMF), dimethyl acetamide (DMA), N-methylpyrrolidone, 1,3-dimethyl-2-imidazolidinone, hexamethylphosphoric triamide (HMPA) and the like; sulfones and sulfoxides such as dimethyl sulfoxide (DMSO), sulfolane,and the like.

In the above mentioned process (e), the reaction temperature can be varied within a substantially wide range. In general, the reaction is carried out at a temperature of from about 0° C. to about 200° C., preferably from 20° C. to about 150° C.

Further, the reaction is carried out under normal pressure, although it is also possible to employ a higher or reduced pressure.

When the above mentioned process (e) according to the present invention is carried out, use is made, for example, of about 1 to 3 mols of sodium azide in a diluent such as dimethyl formamide per mol of the compounds represented by the general formula (VII) to obtain the desired compounds.

As specific examples of the formula (II), in the above-mentioned process (a), there may be mentioned:

1-(2-chloro-3-pyridyl)-5(4H)-tetrazolinone, 1-(2-chloro-4-pyridyl)-5(4H)-tetrazolinone, 1-(2-pyridyl)-5(4H)-tetrazolinone, 1-(3-pyridyl)-5(4H)-tetrazolinone, 1-(4-pyridyl)-5(4H)-tetrazolinone,
1-(3-chloro-2-pyridyl)-5(4H)-tetrazolinone,
1-(4-fluoro-3-pyridyl)-5(4H)-tetrazolinone,
1-(3-chloro-4-pyridyl)-5(4H)-tetrazolinone,
1-(3-bromo-4-pyridyl)-5(4H)-tetrazolinone,
1-(6-chloro-3-pyridyl)-5(4H)-tetrazolinone,
1-(3-methyl-2-pyridyl)-5(4H)-tetrazolinone,
1-(3-fluoro-4-pyridyl)-5(4H)-tetrazolinone,
1-(2-methyl-3-pyridyl)-5(4H)-tetrazolinone,
1-(4-chloro-3-pyridyl)-5(4H)-tetrazolinone,
1-(3-methoxy-2-pyridyl)-5(4H)-tetrazolinone,
1-(4-methyl-3-pyridyl)-5(4H)-tetrazolinone,
1-(2-methylthio-3-pyridyl)-5(4H)-tetrazolinone,
1-(3-methyl-4-pyridyl)-5(4H)-tetrazolinone,
1-(2-trifluoromethyl-3-pyridyl)-5(4H)-tetrazolinone,
1-(2,6-dichloro-3-pyridyl)-5(4H)-tetrazolinone,
1-(3-trifluoromethyl-2-pyridyl)-5(4H)-tetrazolinone,
1-(2-chloro-6-methyl-3-pyridyl)-5(4H)-tetrazolinone,
1-(2-methoxy-3-pyridyl)-5(4H)-tetrazolinone,
1-(2,6-dichloro-4-pyridyl)-5(4H)-tetrazolinone,
1-(4-trifluoromethyl-3-pyridyl)-5(4H)-tetrazolinone,
1-(3,5-dichloro-2-pyridyl)-5(4H)-tetrazolinone,
1-(3-methylthio-4-pyridyl)-5(4H)-tetrazolinone,
1-(5-trifluoromethyl-2-pyridyl)-5(4H)-tetrazolinone,
1-(3,5-dichloro-4-pyridyl)-5(4H)-tetrazolinone,
1-(2-chloro-4-methyl-3-pyridyl)-5(4H)-tetrazolinone,
1-(3-chloro-5-trifluoromethyl-2-pyridyl)-5(4H)-tetrazolinone,
1-(4,6-dimethoxy-2-trifluoromethyl-3-pyridyl)-5(4H)-tetrazolinone,
1-(2,6-dimethyl-3-pyridyl)-5(4H)-tetrazolinone,
1-(6-chloro-2,4-dimethyl-3-pyridyl)-5(4H)-tetrazolinone,
1-(3-ethyl-4-pyridyl)-5(4H)-tetrazolinone,
1-(2-chloro-4,6-dimethyl-3-pyridyl)-5(4H)-tetrazolinone,
1-(5-trifluoromethoxy-2-pyridyl)-5 (4 H)-tetrazolinone,
1-(2,4-dimethyl-3-pyridyl)-5(4H)-tetrazolinone,
1-(3-nitro-2-pyridyl-pyridyl)-5(4H)-tetrazolinone,
1-(3,5-bis(trifluoromethyl)-2-pyridyl)-5(4H)-tetrazolinone, and
1-(2-phenoxy-3-pyridyl)-5(4H)-tetrazolinone, In the process (a), the starting materials of the formula (III) means those based on the above mentioned definition of $R^1$ and $R^2$, and preferably compounds based on the above preferred definitions.

The compounds of the formula (III) are well known in the field of organic chemistry.

As examples of the compounds of the formula (III), the following compounds may be mentioned:

Diisopropylcarbamoyl chloride and bromide,
Diethylcarbamoyl chloride and bromide,
Dimethylcarbamoyl chloride and bromide,
N-methyl-N-ethylcarbamoyl chloride and bromide,
N-methyl-N-n-propylcarbamoyl chloride and bromide,
N-methyl-N-isopropylcarbamoyl chloride and bromide,
N-methyl-N-cyclopropylcarbamoyl chloride and bromide,
N-methyl-N-s-butylcarbamoyl chloride and bromide,
N-methyl-N-cyclopenthylcarbamoyl chloride and bromide,
N-methyl-N-cyclohexylcarbamoyl chloride and bromide,
N-methyl-N-phenylcarbamoyl chloride and bromide,
N-methyl-N-1-methyl-2-propenylcarbamoyl chloride and bromide,
N-ethyl-N-propylcarbamoyl chloride and bromide,
N-ethyl-N-isopropylcarbamoyl chloride and bromide,
N-ethyl-N-cyclopropylcarbamoyl chloride and bromide,
N-ethyl-N-s-butylcarbamoyl chloride and bromide,
N-ethyl-N-cyclopentylcarbamoyl chloride and bromide,
N-ethyl-N-cyclohexylcarbamoyl chloride and bromide,
N-ethyl-N-phenylcarbamoyl chloride and bromide,
N-n-propyl-N-isopropylcarbamoyl chloride and bromide,
N-n-propyl-N-cyclopropylcarbamoyl chloride and bromide,
N-n-propyl-N-s-butylcarbamoyl chloride and bromide,
N-n-propyl-N-cyclopentylcarbamoyl chloride and bromide,
N-n-propyl-N-cyclohexylcarbamoyl chloride and bromide,
N-isopropyl-N-cyclohexylcarbamoyl chloride and bromide,
N-isopropyl-N-phenylcarbamoyl chloride and bromide,
N-isopropyl-N-allylcarbamoyl chloride and bromide,
4-morpholinylcarbamoyl chloride and bromide,
1-(2-methylpiperidine)carbamoyl chloride and bromide,
1-(2,5-dimethylpyrrolidine)carbamoyl chloride and bromide,
1-(2,6-dimethylpiperidine)carbamoyl chloride and bromide,
1-(2-methyl-1,2,3,4-tetrahydroquinoline)carbamoyl chloride and bromide,
1-Pyrrolidinylcarbamoyl chloride and bromide,
1-Piperidylacrbamoyl chloeide and bromide, and
1-(2,5-dimethyl-3-pyrroline)carbamoyl and bromide, In carrying out the process (a) mentioned above, use may be made, as suitable diluent, of any inert solvent.

Examples of such diluents are aliphatic, cycloaliphatic and aromatic, optionally chlorinated, hydrocarbons such as pentane, hexane, cyclohexane, petroleum ether, ligroin, benzene, toluene, xylene, dichloromethane, chloroform, carbon tetrachloride, 1,2-dichloroethane, chlorobenzene, dichlorobenzene, and the like; ethers such as diethyl ether, methyl ethyl ether, diisopropyl ether, dibutyl ether, dioxane, dimethoxyethane(DME), tetrahydrofurane (THF) dimethylene glycol dimethyl ether and the like; nitriles such as acetonitrile, propionitrile,and the like; acid amides such as dimethyl formamide (DMF), dimethyl acetamide (DMA), N-methylpyrrolidone, 1,3-dimethyl-2-imidazolidinone, hexamethylphosphoric triamide (HMPA),and the like; sulfones and sulfoxides such as dimethyl sulfoxide (DMSO), sulfolane and the like; and bases such as pyridine.

The process (a) according to the invention is carried out preferably in the presence of acid or acid binder.

As example s of such acid binder there may be mentioned:

inorganic bases including hydroxide, carbonate, bicarbonate and alcoholate of alkali metals such as, for example, sodium hydrogen carbonate, potassium hydrogen carbonate, sodium carbonate, potassium carbonate, and the like, inorganic alkali metal amide including lithium amide, sodium amide, potassium amide, and the lik organic bases including tertiary amines, dialkylaminoanilines and pyridines such as, for example, triethylamine, tributylamine, 1,1,4,4-tetramethylenediamine (TMEDA), N,N-dimethylaniline, N,N-diethylaniline, pyridine, 4-dimethylaminopyridine (DMAP), 1,4-diaza-bicyclo-[2,2,2] octane (DABCO), 1,8-diaza-bicyclo[5,4,0]-undec-7-ene (DBU) and the like, organic lithium compounds including methyllithium, n-butyllithium, sec-butyllithium, tert-butyllithium, phenyllithium, dimethyl copper lithium, lithiumdiisopropylamide, lithiumcyclohexylisopropylamide, lithiumdicyclohexylamide, n-butyllithium DABCO n-butyllithium TMEDA.

In the above mentioned process (a), the reaction temperature can be varied within a substantially wide range. In general, the reaction is carried out at a temperature of from about −30° C. to about 200° C., preferably from −20° C. to about 130° C.

Further, the reaction is carried out under normal pressure, although it is also possible to employ a higher or reduced pressure.

When the above mentioned process (a) according to the present invention is carried out, use is made, for example, of about 1.0 to 1.5 mols of the compound of the formula (III) in a diluent such as toluene per mol of the compounds represented by the general formula (II) in the presence of 1 to 1.5 mols of the acid binder to obtain the desired compounds.

The active compounds according to the invention can be used as defoliants, desiccants, agents for destroying broad-leaved plants and, especially, as weedkillers.

By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted into the customary formulations, such as solutions, emulsions, wettable powders, suspensions, powders, foams, pastes, granules, tablets, aerosols, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carders, there are suitable in the main, aromatic hydrocarbons, such as xylene, toluene or alkyl napthalenes, chlorinated aromatic or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carders them may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules them may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-acid esters, polyoxyethylene-alcohol ethers, for example alkylaryl polyglycol ethers, alkyl sulphonates, alkyl sulphates, aryl sulphonates as well as albumin hydrolysis products.

Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulation.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese boron, copper, cobalt, molybdenum and zinc.

The formulations in general contain from 0.1 to 95 per cent by weight of active compound, preferably from 0.5 to 90 per cent by weight.

The active compounds according to the invention, as such or in the form of their formulations, can also be used, for combating weeds, as mixtures with known herbicides, finished formulations or tank mixes being possible.

Mixtures with other known active compounds, such as herbicides, fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules.

They are used in the customary manner, for example by watering, spraying, atomizing or scattering.

The active compounds according to the invention can be applied either before or after emergence of the plants. They can also be incorporated into the soil before sowing. They are used, in particular, after emergence of the plants.

The amount of active compound used can vary within a substantial range. It depends essentially on the nature of the desired effect. In general, the amounts used are between 0.001 and 10 kg of active compound per hectare of soil surface, preferably between 0.01 and 5 kg per ha.

The preparation and use of the active compounds according to the invention can be seen from the following examples.

EXAMPLE 1

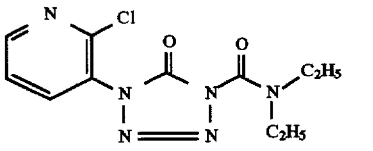

Compound No. 1

1-(2-chloro-3-pyridyl)-5(4H)-tetrazolinone (1.0 g), diethylcarbamoyl chloride (0.7 g) and 4-dimethylaminopyridne (0.7 g) were suspended in toluene (15 ml). The resulting suspension was heated under reflux for 6 hours. The salts were removed by filtration, and the solvent was distilled off under reduced pressure. The resulting residue was subjected to a silica gel chromatography (chloroform) so that 1-(2-chloro-3-pyridyl)-4-(N,N-diethylcarbamoyl)-5(4H)-tetrazolinone (1.3 g) was obtained.

$n_D^{20}$=1.5511

Further compounds obtainable by the above-mentioned reaction procedure are shown in Table 3-1.

TABLE 3-1

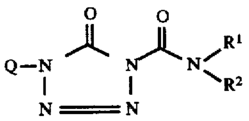

| Compound No. | Q | $R^1$ | $R^2$ | Physical Constant |
|---|---|---|---|---|
| 2 | Q2 | ethyl | ethyl | $n_D^{20}$ = 1.5426 |
| 3 | Q3 | ethyl | ethyl | m.p. 72.5–75° C. |
| 4 | Q5 | methyl | isopropyl | m.p. 99.5–101° C. |
| 5 | Q5 | ethyl | isopropyl | m.p. 87.5–89.5° C. |
| 6 | Q5 | ethyl | cyclohexyl | m.p. 56.5–60° C. |
| 7 | Q5 | allyl | allyl | $n_D^{20}$ = 1.5616 |
| 8 | Q5 | propargyl | propargyl | m.p. 142–145.5° C. |
| 9 | Q7 | ethyl | ethyl | m.p. 61–62° C. |
| 10 | Q11 | methyl | isopropyl | $n_D^{20}$ = 1.5561 |

TABLE 3-1-continued

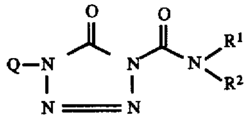

| Compound No. | Q | $R^1$ | $R^2$ | Physical Constant |
|---|---|---|---|---|
| 11 | Q11 | ethyl | ethyl | m.p 70–71.5° C. |
| 12 | Q12 | ethyl | ethyl | m.p. 63–67° C. |
| 13 | Q12 | ethyl | isopropyl | $n_D^{20}$ = 1.5579 |
| 14 | Q14 | ethyl | ethyl | m.p. 51.5–53.5° C. |
| 15 | Q14 | ethyl | isopropyl | $n_D^{20}$ = 1.5388 |

TABLE 3-2

| Compound No. | Q | $R^1$ | $R^2$ | Physical Constant |
|---|---|---|---|---|
| 16 | Q19 | methyl | isopropyl | m.p. 115.5–118.5° C. |
| 17 | Q19 | ethyl | ethyl | m.p. 68.5–72.5° C. |
| 18 | Q19 | ethyl | isopropyl | $n^{20}_D$ = 1.5685 |
| 19 | Q24 | ethyl | ethyl | $n^{20}_D$ = 1.5032 |
| 20 | Q26 | methyl | isopropyl | m.p. 113.5–115.5° C. |
| 21 | Q26 | ethyl | ethyl | m.p. 104–109.5° C. |
| 22 | Q26 | ethyl | isopropyl | m.p. 105–109° C. |
| 23 | Q27 | ethyl | ethyl | m.p. 119.5–120.5° C. |
| 24 | Q29 | methyl | isopropyl | m.p. 112–115° C. |
| 25 | Q29 | ethyl | ethyl | m.p. 105.5–107.5° C. |
| 26 | Q29 | ethyl | isopropyl | m.p. 126–128° C. |
| 27 | Q30 | methyl | isopropyl | m.p. 124.5–127.5° C. |
| 28 | Q30 | ethyl | ethyl | $n^{20}_D$ = 1.5442 |
| 29 | Q30 | ethyl | isopropyl | $n^{20}_D$ = 1.5397 |
| 30 | Q41 | ethyl | ethyl | m.p. 87.5–90.5° C. |

Synthesis of starting materials

EXAMPLE 2

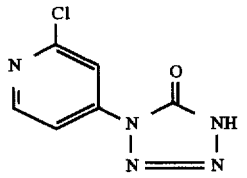

2-Chloroisonicotinic acid (4.7 g) and thionyl chloride (10.0 g) were mixed and the resulting mixture was heated under reflux for 2 hours. The excess thionyl chloride was distilled off under reduced pressure, and trimethylsilyl azide (10.0 g) was added to the residue thus obtained. The resulting mixture was heated under reflux for 24 hours, and the excess trimethylsilyl azide was distilled off under reduced pressure and then methanol was added to the residue thus obtained. Thereafter, the methanol was distilled off and the resultant residue was subjected to a silica gel chromatography, using chloroform: ethanol=15:1 , so that 1-(2-chloro-4-pyridyl)-5(4H)-tetrazolinone (4.6 g) was obtained.

m.p. 182.5°–184° C. (decomposition).

1-(3-Pyridyl)-5(4H)-tetrazolinone (1.0 g) was obtained by the same process as was used in the Example 2 with the exception that nicotinic acid (1.1 g) was used instead of 2-chloroisonicotinic acid.

m.p. 201.5°–202.5° C.

1-(4-Pyridyl)-5(4H)-tetrazolinone (3.3 g) was obtained by the same process as was used in the Example 2 with the exception that isonicotinic acid (3.5 g) was used instead of 2-chloroisonicotinic acid.

m.p. more than 300° C.

1-(6-Chloro-3-pyridyl)-5(4H)-tetrazolinone (3.8 g) was obtained by the same process as was used in the Example 2 with the exception that 6-chloronicotinic acid (3.5 g) was used instead of 2-chloroisonicotinic acid.

m.p. 212°-212.5° C.

1-(3-Chloro-4-pyridyl)-5(4H)-tetrazolinone (1.8 g) was obtained by the same process as was used in the Example 2 with the exception that 3-chloroisonicotinic acid (4.7 g) was used instead of 2-chloroisonicotinic acid.

m.p. 176°-178.5° C. (decomposition).

1-(2-Methyl-3-pyridyl)-5(4H)-tetrazolinone (3.9 g) was obtained by the same process as was used in the Example 2 with the exception that, 2-methyl-nicotinic acid (4.1 g) was used instead of 2-chloroisonicotinic acid.

m.p. 174.5°-176° C. (decomposition).

1-(2-Methylthio-3-pyridyl)-5(4H)-tetrazolinone (4.5 g) was obtained by the same process as was used in the Example 2 with the exception that 2-methylthionicotinic acid (5.1 g) was used instead of 2-chloroisonicotinic acid.

m.p. 168° C. (decomposition).

1-(2-Chloro-6-methyl-3-pyridyl)-5(4H)-tetrazolinone (4.3 g) was obtained by the same process as was used in the Example 2 with the exception that 2-chloro-6-methylnicotinic acid (4.9 g) was used instead of 2-chloroisonicotinic acid.

m.p. 196°-197.5° C.

1-(4-trifluoromethyl-3-pyridyl)-5(4H)-tetrazolinone (1.2 g) was obtained by the same process as was used in the Example 2 with the exception that 4-trifluoromethylnicoticic acid (5.0 g) was used instead of 2-chloroisonicotinic acid.

m.p. 129.5°-132.5° C.

1-(2,6-Dichloro-4-pyridyl)-5(4H)-tetrazolinone (3.5 g) was obtained by the same process as was used in the Example 2 with the exception that 2,6-dichloroisonicotinic acid (6.8 g) was used instead of 2-chloroisonicotinic acid.

m.p. 123°-128° C.

EXAMPLE 3

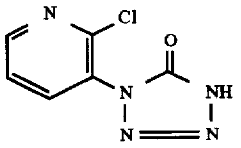

2-Chloro-3-pyridyl isocyanate (3.1 g) was mixed with trimethylsilyl azide (3.5 g), and the resulting mixture was heated under reflux for 20 hours. The excess trimethylsilyl azide was distilled off under reduced pressure, and methanol was added to the residue thus obtained. Thereafter, the methanol was distilled off, and the resultant residue was subjected to a silica gel column chromatography, using chloroform; ethanol=15:1, so that 1-(2-chloro-3-pyridyl)-5(4H)-tetrazolinone (3.0 g) was obtained.

m.p. 177.5°-178.5° C.

1-(2,6-Dichloro-4-pyridyl)-5(4H)-tetrazolinone (3.7 g) was obtained by the same process as was used in the Example 3 with the exception that 2,6-dichloro-4-pyridyl isocyanate (3.2 g) was used instead of 2-chloro-3-pyridyl isocyanate.

m.p. 191°-191.5° C.

1-(2,6-Dichloro-3-pyridyl)-5(4H)-tetrazolinone (3.5 g) was obtained by the same process as was used in the Example 3 with the exception that 2,6-dichloro-3-pyridyl isocyanate (5.7 g) was used instead of 2-chloro-3-pyridyl isocyanate.

m.p. 176°-177° C.

1-(2-Chloro-4-methyl-3-pyridyl)-5(4H)-tetrazolinone (4.1 g) was obtained by the same process as was used in the Example 3 with the exception that 2-chloro-4-methyl-3-pyridyl isocyanate (3.4 g) was used instead of 2-chloro-3-pyridyl isocyanate.

m.p. 160°-162° C.

EXAMPLE 4

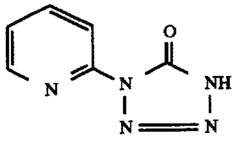

1-(2-Pyridyl)-5-methanesulfonyl-tetrazole (0.90 g) and tetrahydrofurane (15 ml) were added to water (1 ml) containing dissolved sodium hydroxide (0.80 g) and the resulting mixture was heated under reflux for 3 hours. After solvent was distilled off under reduced pressure, the resultant residue was subjected to a silica gel column chromatography, using chloroform: ethanol=15:1, so that 1-(2-pyridyl)-5(4H)-tetrazolinone (0.2 g) was obtained.

m.p. 147-147.5 ° C. (decomposition)

EXAMPLE 5

Starting material of Example 4

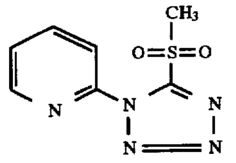

1-(2-Pyridyl)-5-methylthiotetrazole (1.5 g), OXONE® (9.6 g), water (15 ml) and ethanol (45 ml) were mixed and the resulting mixture was stirred at room temperature for 24 hours. After solvent was distilled off under reduced pressure, the resultant residue was subjected to a silica gel column chromatography (chloroform) so that 1-(2-pyridyl)-5-methanesulfonyl-tetrazole (1.0 g) was obtained.

m.p. 110.5°-112° C.

EXAMPLE 6

Starting material of Example 5

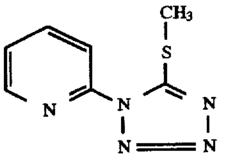

4-(2-Pyridyl)-3-thiosemicarbazide (12.2 g), suspended to water (30 ml), and dimethylsufate (9.15 g) was added to the suspension. The resulting suspension was stirred for 3 hours. To this solution concentrated hydrochloric acid (30 ml) was added and the solution was cooled to 0° C. An aqueous solution (15 ml) of sodium nitrite (5.8 g) was added dropwise to the solution while maintaining the temperature and, after having stirred at 0° C. for 2 hours, the solution was neutralized by potassium carbonate and then extracted with chloroform. After drying with anhydrous sodium sulfate, the residue was subject to a silica gel column chromatography (chloroform) so that 1-(2-pyridyl)-5-methylthiotetrazole (2.0 g) was obtained.

m.p. 106°–108° C.

EXAMPLE 7

Starting material of Example 6

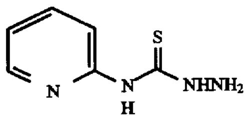

Methyl N-(2-pyridyl)dithiocarbamate (22.6 g), hydrazine monohydrate (12.3 g) and ethanol (300 ml) were mixed and the resulting mixture was heated under reflux for 3 hours. After distilling off the solvent under reduced pressure, water was added to the residue thus obtained, and a deposited material was obtained by filtration and dried by air, so that 4-(2-pyridyl)-3-thiosemicarbazide (18.9 g) was obtained.

m.p. 192.5°–193° C.

EXAMPLE 8

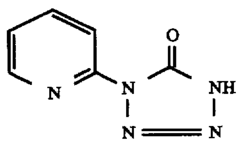

Anhydrous aluminum chloride (8.6 g) was added to dimethylformamide (50 ml) under ice-cooling and the resulting mixture was stirred for 15 minutes. Sodium azide (3.8 g) was further added to that mixture and the mixture obtained was stirred for 15 minutes. After said stirring, phenyl N-(2-pyridyl)carbamate (6.3 g) was added to the mixture, and the resulting mixture was stirred at 80° C. for 10 hours. The reaction solution was added to the mixture of sodium nitrite (4 g), water (500 ml) and ice (250 g). After acidifying with 10% hydrochloric acid solution (until coloring the potassium iodide starch paper), the solution was extracted by ethyl acetate, and then the ethyl acetate phase obtained was dried with sodium sulfate. Thereafter solvent was distilled off under reduced pressure, the resultant residue was subjected to a silica gel column chromatography, so that 1-(2-pyridyl)-5(4H)-tetrazolinone was obtained (0.2 g).

m.p. 147°–147.5° C. (decomposition).

EXAMPLE 9

Starting material of the Example 8

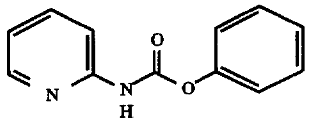

2-Aminopyridine (9.4 g) was dissolved in pyridine (150 ml) and phenylchloroformate (15.7 g) was added dropwise to the resulting solution under cooling at 0° C. After stirring at 0° C. for 2 hours, the solvent was distilled off under reduced pressure, and water was added to the residue thus obtained. Deposited crystals were separated by filtration and dried by air to obtain phenyl N-(2-pyridyl) carbamate (18.9 g).

m.p. 161°–162.5° C.

EXAMPLE 10

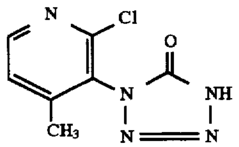

3-Amino-2-chloro-4-methylpyridine (4.3 g) was added to a solution of trichloro-methyl chloformate (6.0 g) in ethyl acetate (100 ml) at 0° to 5° C. with stirring and the mixture was refluxed under heating for 6 hours. After removal of the solvent under reduced pressure, 2-chloro-4-methyl-3-pyridylisocyanate (4.9 g) was obtained. A mixture of 2-chloro-4-methyl-3-pyridylisocyanate (4.9 i) and trimethylsilyl azide (11 g) was refluxed under heating for 30 hours. After removal of excess trimethylsilyl azide under reduced pressure, methanol was added to the resulting residue. Thereafter, the methanol was distilled off under reduced pressure. The resulting residue was purified by flash column chromatography (eluent chloroform:ethanol=15:1) to obtain the desired 1-(2-chloro-4-methyl-3-pyridyl)-5(4H)-tetrazolinone (3.0 g). m.p. 160°–162° C.

Biological tests

EXAMPLE 11

(Pre-emergence soil treatment test on upland weeds)

Formulation of Active Compounds

Carrier: 5 parts by weight of acetone

Emulsifier: 1 part by weight of benzyloxy polyglycol ether

To prepare suitable formulations, 1 part by weight of each of the active compounds was mixed with the above-stated amounts of the carrier and the emulsifier, and the resulting emulsifiable concentrate was then diluted with water to the desired concentrations.

Test Procedure

In a greenhouse, a number of test pots each having an area of 120 $cm^2$ were charged with soil taken from a cultivated field. Seeds of barnyard-grass and wild amaranth (*Amaranthus blitum*) were sown onto the soil surfaces in the respective test pots and each of the thus sown soil surfaces was covered with a soil layer.

Predetermined dosages of the active compounds of formulations prepared as mentioned above were uniformly sprayed onto the soil surface in the respective test pots.

Four weeks after the spraying of the active compound formulations, the herbicidal effects on the weeds were determined. The herbicidal effects were rated according to the following assessment:

Completely killed 100%

Condition equivalent to non-treated pots 0%

In the above-mentioned test, for example, compound Nos. 1, 3, 4, 5, 11, 12, 13, 15, 17, 18, 21, 22, 25 and 26 according to the present invention showed 100% herbicidal effect against barnyard-grass and wild amaranth at a dosage of 1.0 kg/ha.

EXAMPLE 12

(Post-emergence foliage treatment on upland weeds)

Test Procedure

In a greenhouse, a number of test pots each having an area of 120 $cm^2$ were charged with soil taken from a cultivated field. Seeds of barnyard-grass and wild amaranth (Amaranthus blitum) were sown onto the soil surfaces in the respective test pots and each of the thus sown soil surfaces was covered with a soil layer.

Ten days after sowing (average 2 leaf stage of weeds), predetermined dosages of active compounds of formulations prepared as in Example 10 were uniformly sprayed onto the foliage portions of the test plants in the respective test pots.

Three weeks after the spraying of the active compound formulations, the herbicidal effects on the weeds were determined.

In the above mentioned test, for example, the compounds Nos. 1,4,13,15 and 22 according to the present invention showed 100% herbicidal effect against barnyard-grass and wild amaranth at a dosage of 1.0 kg/ha.

It will be appreciated that the instant specification and the claims are set forth by way of illustration and not limitation, and that various modification and changes may be made without departing from the spirit and scope of the present invention.

We claim:

1. A pyridyltetrazolonone of the formula

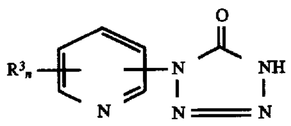

in which n is 0, 1, 2, or 3, and $R^3$ each independently is nitro, halogen, alkyl, haloalkyl, alkoxy, alkylthio or phenoxy.

2. A compound according to claim 1, in which $R^3$ is nitro, fluoro, chloro, bromo, $C_{1-4}$ alkyl, $C_{1-4}$ haloalkyl, $C_{1-4}$ alkoxy, $C_{1-4}$ haloalkoxy, $C_{1-4}$ alkylthio or phenoxy.

3. A compound according to claim 1, in which n is 0, 1 or 2.

* * * * *

UNITED STATES PATENT AND TRADEMARK OFFICE

CERTIFICATE OF CORRECTION

PATENT NO. : 5,710,278

DATED : Jan. 20, 1998

INVENTOR(S) : Goto, et al.

It is certified that error appears in the above-indentified patent and that said Letters Patent is hereby corrected as shown below:

Title Page. Related U.S. Application Data [62]: After " Ser. No. 498,736, " delete " Jun. 6, 1995 " and substitute -- Jul. 6, 1995--

Signed and Sealed this

Twenty-first Day of April, 1998

Attest:

BRUCE LEHMAN

Attesting Officer

Commissioner of Patents and Trademarks